(12) United States Patent
Pasha

(10) Patent No.: US 11,857,346 B2
(45) Date of Patent: Jan. 2, 2024

(54) SYSTEMS AND METHODS FOR REAL-TIME MONITORING OF BONE CORRECTION

(71) Applicant: Warsaw Orthopedic, Inc., Warsaw, IN (US)

(72) Inventor: Saba Pasha, Houston, TX (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 219 days.

(21) Appl. No.: 17/329,974

(22) Filed: May 25, 2021

(65) Prior Publication Data
US 2022/0378370 A1    Dec. 1, 2022

(51) Int. Cl.
*A61B 5/00* (2006.01)
*G16H 50/20* (2018.01)
(Continued)

(52) U.S. Cl.
CPC .............. *A61B 5/686* (2013.01); *A61B 5/091* (2013.01); *A61B 5/4504* (2013.01);
(Continued)

(58) Field of Classification Search
CPC . A61B 5/4504; A61B 5/7264; A61B 17/7014; A61B 17/7016; A61B 17/663; A61B 17/688; A61B 17/7017; A61B 17/7216; A61B 17/8071; A61B 5/4851; A61B 5/6878; A61B 17/66; A61B 5/686;
(Continued)

(56) References Cited

U.S. PATENT DOCUMENTS 6,485,491 B1   11/2002   Farris et al.
8,057,519 B2   11/2011   Justis et al.
(Continued)

FOREIGN PATENT DOCUMENTS

KR   102066839 B1   1/2020
WO   201129855 A2   10/2011
(Continued)

OTHER PUBLICATIONS

European Search Report in Application No. 22171117.9 dated Oct. 26, 2022.
(Continued)

*Primary Examiner* — Eric F Winakur
*Assistant Examiner* — Elina Sohyun Ahn
(74) *Attorney, Agent, or Firm* — FOX ROTHSCHILD LLP

(57) ABSTRACT

Systems and methods to monitor and track the treatment of bones using a bone correction system are provided. The method includes implanting growth modulating implants of a bone correction system in two or more bones of a patient. Each growth modulating implant includes an implant body having at least one sensor device embedded in the implant body. The method includes receiving sensor data from the sensor devices and determining an operational status of the growth modulating implants, based on the received sensor data. The method includes determining, by the processor, a longitudinal growth or growth rate between the two or more bones, based on the received sensor data and causing a display device to selectively display a graphical user interface (GUI) representative of at least one of the longitudinal growth and the growth rate of the patient.

18 Claims, 26 Drawing Sheets

(51) Int. Cl.
*A61B 5/091* (2006.01)
*A61B 17/70* (2006.01)
*A61B 17/00* (2006.01)

(52) U.S. Cl.
CPC .......... *A61B 5/6898* (2013.01); *A61B 5/7267* (2013.01); *A61B 5/746* (2013.01); *A61B 5/7435* (2013.01); *A61B 17/7002* (2013.01); *G16H 50/20* (2018.01); *A61B 2017/00022* (2013.01); *A61B 2017/00221* (2013.01); *A61B 2503/06* (2013.01); *A61B 2562/0261* (2013.01)

(58) Field of Classification Search
CPC . A61B 17/70; A61B 17/7002; A61B 17/7032; A61B 17/7049; A61B 17/7091; A61B 2090/037; A61B 2017/00221; A61B 2090/064; A61B 2090/066; A61B 2090/065; A61B 2562/0261; A61B 5/4566; A61B 17/68; A61B 2017/681; A61B 5/4509; A61B 5/091; A61B 2017/00022; A61B 2017/00402; A61B 5/1072; A61B 5/4836
See application file for complete search history.

(56) References Cited

U.S. PATENT DOCUMENTS

| | | | |
|---|---|---|---|
| 9,011,499 B1 | 4/2015 | Kiester | |
| 9,220,536 B2 | 12/2015 | Skaggs | |
| 9,445,720 B2 | 9/2016 | Janna et al. | |
| 10,314,619 B2 | 6/2019 | Roschak et al. | |
| 10,362,982 B2 | 7/2019 | Stevenson et al. | |
| 10,456,171 B2 | 10/2019 | Kawakami et al. | |
| 2010/0191088 A1* | 7/2010 | Anderson | A61B 34/20 606/300 |
| 2014/0194932 A1 | 7/2014 | Bruneau et al. | |
| 2016/0004820 A1* | 1/2016 | Moore | G16H 15/00 705/3 |
| 2017/0231559 A1 | 8/2017 | Cuevas et al. | |
| 2019/0254712 A1* | 8/2019 | Roschak | A61B 17/7016 |
| 2020/0022740 A1 | 1/2020 | Benson et al. | |
| 2020/0054215 A1 | 2/2020 | Roche | |
| 2020/0069247 A1 | 3/2020 | Hunter | |
| 2021/0307786 A1* | 10/2021 | Ross | A61B 5/0031 |

FOREIGN PATENT DOCUMENTS

| | | |
|---|---|---|
| WO | 2016065205 A1 | 4/2016 |
| WO | 2018017591 A1 | 1/2018 |
| WO | 2018017591 A9 | 4/2018 |
| WO | 2020055874 A1 | 3/2020 |

OTHER PUBLICATIONS

Ian A. F. Stokes, et al., Vertebral Height Growth Predominates Over Intervertebral Disc Height Growth in Adolescents With Scoliosis, NIH Public Access Author Manuscript, 10PP, Spine (Phila Pa 1976). Jun. 15, 2006; 31(14): 16000-1604. DOI:10.1097/01.FRS.0000222008.15750.1F.

Mohamed Yehia, et al., Dual Growing Rod Technique for the Treatment of Early-Onset Scoliosis, Life Science Journal 2020; 17(2), HTTPS://www.lifesciencesite.com, pp. 58-64.

Daniel Garcia-Martinez et al., Ribcage Measurements Indicate Greater Lung Capacity in Neanderthals and Lower Pleistocene Hominins Compared to Modern Humans; Communications Biology (2018)1:117, www.Nature.com/Commsbio, Doi: 10.1038/S42003-018-0125-4.

Juan A. Sanchis-Gimeno, et al., Association Between Ribs Shape and Pulmonary Function in Patients With Osteogenesis Imperfecta, Journal of Advances Research 21 (2020) 177-185, HTTPS://doi.org/10/1016/j.jare.2019.10.007.

Pavilio Piccioni et al., Lung Function Changes From Childhood To Adolescence: a Seven-Year Follow-Up Study, BMC Pulmonary Medicine (2015) 15:31, DOI 10.1186/S 12890-015-0028-9, 8PP.

Theodoros B. Grivas, et al., A Segmental Analysis of Thoracic Shape in Ches Radiographs of Children. Changes Related to Spinal Level, Age, Sex, Side and Significance for Lung Growth and Scoliosis, J. Anat. (1991), 178, pp. 21-38.

Alain Dimeglio, et al., The Growing Spine: How Spinal Deformities Influence Normal Spine and Thoracic Cage Growth, Eur Spine J (2012) 21:64-70, DOI 10.1007/S00586-011-1983-3.

Carlos King Ho Wong, et al. Traditional Growing Rod Versus Magnetically Controlled Growing Rod for Treatment of Early Onset Scoliosis: Cost Analysis From Implantation Till Skeletal Maturity, Journal of Orthopaedic Surgery 25(2) 1-10, DOI: 10.1177/2309499017705022, 2017.

Paula M. Kelly, et al., Lower-Limb Growth: How Predictable Are Predictions?, J. Child Orthop (2008) 2:407-415, DOI 10.1007/S11832-008-0119-8.

Saba Pasha, et al., Contouring the Magnetically Controlled Frowing Rods: Impact on Expansion Capacity and Proximal Junctional Kyphosis; Ruropean Journal of Orthopeadic Surgery and Traumatology (2021) 31:79-84, HTTPS://doi.org/101007/S00590-020-02743-X.

\* cited by examiner

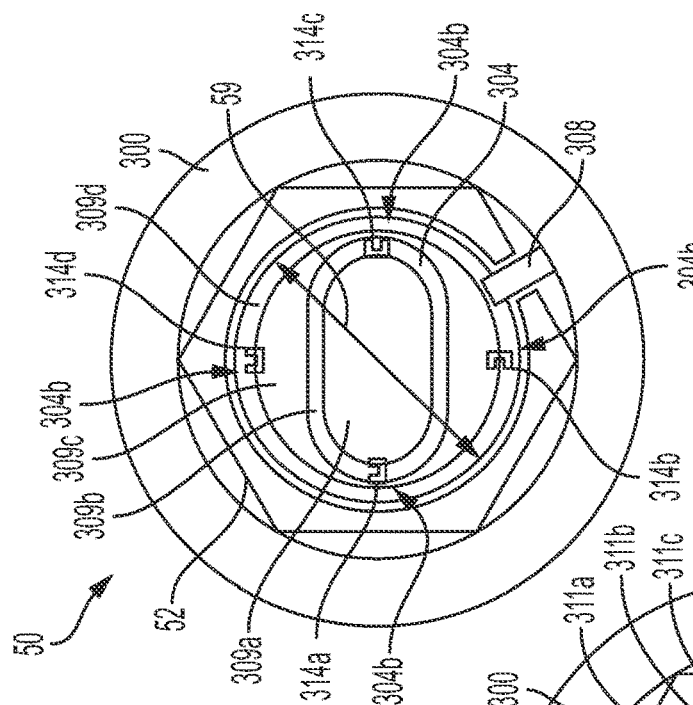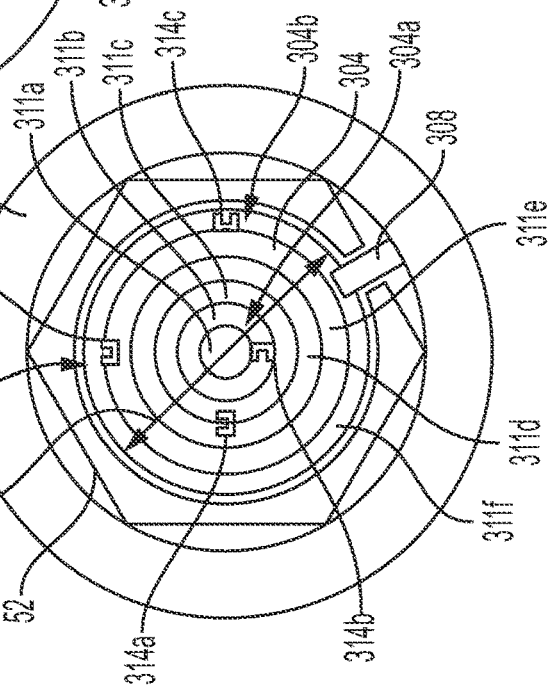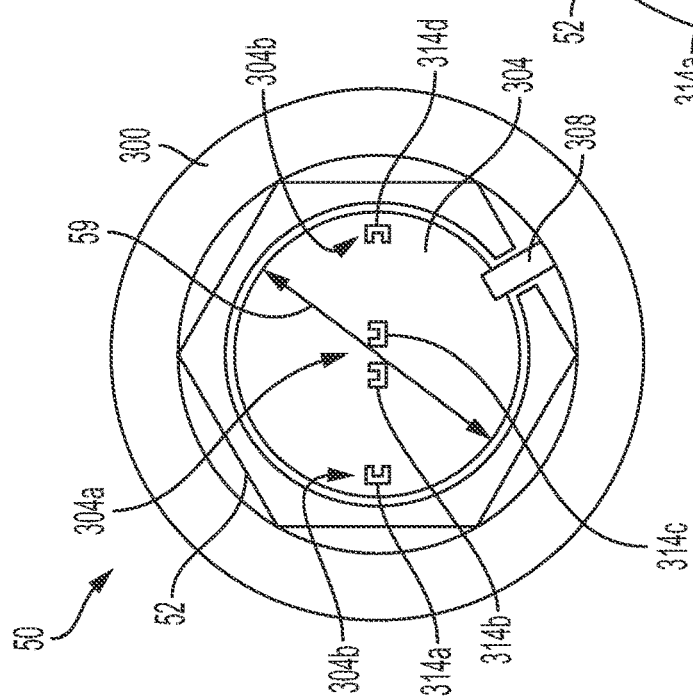

SYSTEMS AND METHODS FOR REAL-TIME MONITORING OF BONE CORRECTION

TECHNICAL FIELD

The present disclosure generally relates to systems and methods for real-time monitoring of bone or spinal correction.

BACKGROUND

Treatment of spinal disorders, such as degenerative disc disease, disc herniation, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members, pelvis, or ribs to assist with the treatment of a spinal disorder. Longitudinal members may provide a stable, rigid column that helps bones to fuse and may redirect stresses over a wider area away from a damaged or defective region. Also, rigid longitudinal members may help in spinal alignment. Similarly, tools that expand the rib cage and lung space may treat spinal deformities, primary or secondary to the chest wall deformities and abnormalities.

Screw assemblies may be used to connect a longitudinal member to a vertebral member. A screw assembly may include a pedicle screw, hook, or other connector and/or a set screw, among other components. A pedicle screw can be placed in, above and/or below vertebral members that were fused, and a longitudinal member can be used to connect the pedicle screws, which inhibits or controls movement. A set screw can be used to secure the connection of a longitudinal member and a pedicle screw, hook or other connector. However, the connection force and continued integrity of the connection between a longitudinal member and a pedicle screw or other connector can be challenging to monitor during and after implantation. In addition, it is difficult to monitor that a proper or acceptable or any force is maintained between a set screw and a longitudinal member.

Spinal care in pediatric spinal or chest wall pathologies aims to conserve the natural spinal growth. Growth enabling spinal surgeries correct or minimize the deformity in a growing spine, postponing the fusion surgery to a later age when the spinal growth is completed, if additional correction is still needed. Such systems allow modulating the growth by differential growth on the concave and convex side of the spine or allowing gradual growth by extending the rod, proportioned to the child's growth rate or other developmental needs such as respiratory function.

Currently, either a fixed interval for rod expansion or clinical imaging for monitoring the growth modulating implants such as a tether is used. A fixed interval for rod expansion may result in over treatment, meaning expanding the rod to a length that exceed the spinal growth or under treatment meaning delayed expansion of the rod resulting in possible curve progression. A delayed detection of the fracture/rupture/or any other changes in the growth modulating implant system such as tethers may be left undetected for several months until the upcoming clinical visit resulting in suboptimal spinal growth or spinal deformity progression.

This disclosure describes an improvement over these prior art technologies.

SUMMARY

The techniques of this disclosure generally relate to systems and methods including a bone correction system having a growth monitoring sensing system, for example that may be implanted to monitor the growth, differential growth and/or growth rate of two or more bones, or lung capacity and function and an operational status of the sensing system.

In one aspect, the present disclosure provides a method that includes implanting growth modulating implants of a bone correction system in two or more bones of a patient. Each growth modulating implant includes an implant body having at least one sensor device embedded in the implant body. The method includes receiving, by a processor, sensor data from the sensor devices associated with the two or more bones; and determining, by the processor, an operational status of the growth modulating implants, based on the received sensor data. The method includes determining, by the processor, a longitudinal growth or growth rate between the two or more bones, based on the received sensor data; and causing, by the processor, a display device to selectively display a graphical user interface (GUI) representative of at least one of the longitudinal growth and the growth rate of the patient.

In another aspect, the disclosure provides a system is provided that includes a bone correction system comprising growth modulating implants being configured to be implanted in two or more bones and a growth monitoring (GM) sensing system. The GM sensing system may include at least one sensor embedded each growth modulating implant. The system includes an electronic device that comprises a processor and a non-transitory and tangible computer readable storage medium having programming instructions stored thereon, which when executed causes the processor to: receive sensor data from the sensor devices associated with the two or more bones; determine an operational status of the growth modulating implants, based on the received sensor data; determine a longitudinal growth or growth rate between the two or more bones, based on the received sensor data; and cause a display device to selectively display a graphical user interface (GUI) representative of at least one of the longitudinal growth, the growth rate of the patient.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIGS. 15C-15E illustrate bottom views taken at cross-section A-A in FIG. 15A of sensors positioned on the load sensing assembly according to an embodiment.

DETAILED DESCRIPTION

Figure 1:
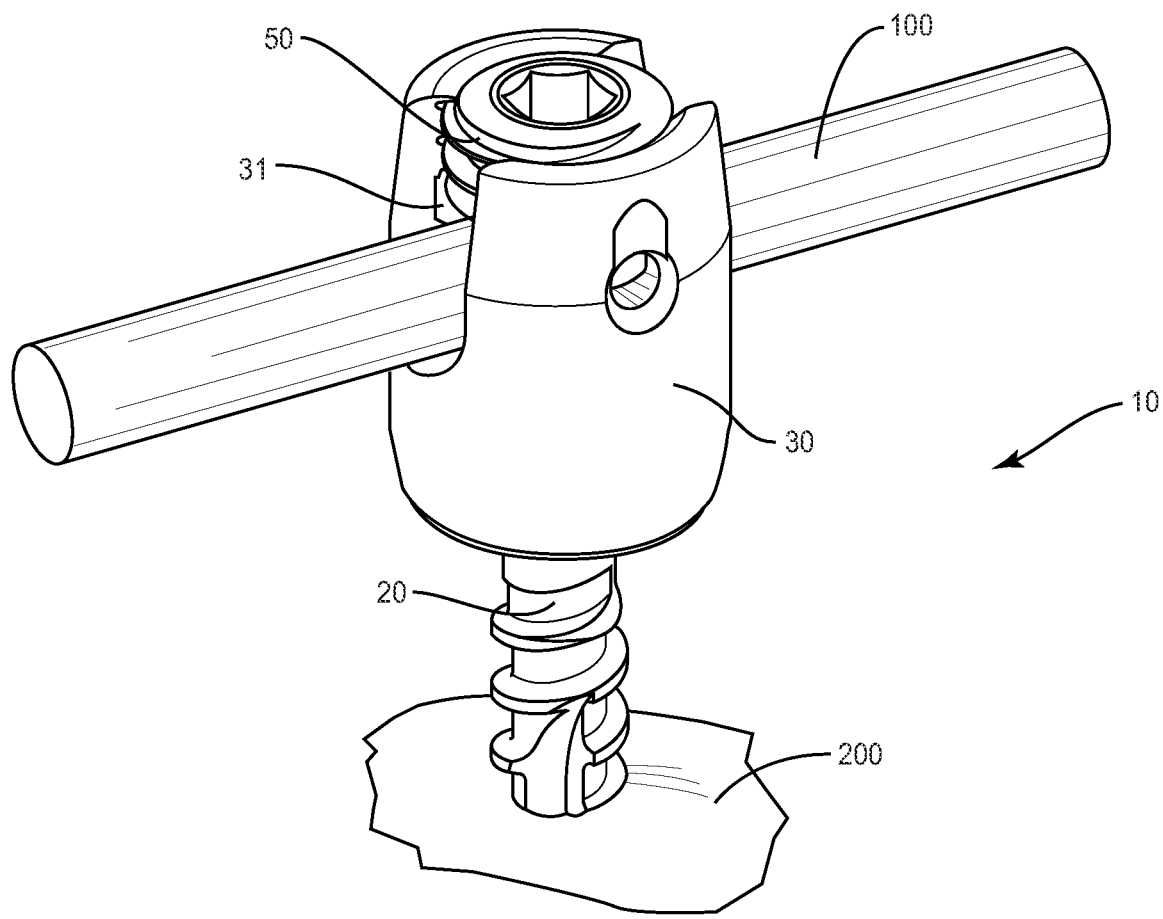
FIG. 1 illustrates an example anchoring assembly and longitudinal member according to an embodiment.

The exemplary embodiments of the surgical system and related method of use disclosed are in terms of medical devices for the treatment of musculoskeletal disorders and more particularly, in terms of growth modulating implants including fixation screws for the treatment of a deformity by monitoring the growth modulating implants in real-time to determine longitudinal growth, growth rate, differential growth or lung capacity, for example, and methods of monitoring the growth modulating implants, implant operational status and patient deformity.

The exemplary embodiments of the surgical system and related methods of use disclosed are discussed in terms of medical devices for the treatment of musculoskeletal disorders and more particularly, in terms of a vertebral fixation screws, including for example pedicle screws, as well as hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of load sensing systems include, for example, U.S. Pat. Nos. 6,485,491 and 8,057,519, all incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral pedicle screw system and related components and methods of employing the vertebral pedicle screw in accordance with the principles of the present disclosure. Reference is made in detail to the exemplary embodiments of the present disclosure, which are illustrated in the accompanying figures.

The components of the vertebral pedicle screw system described herein can be fabricated from biologically acceptable materials suitable for medical applications, including metals, synthetic polymers, ceramics and bone material and/or their composites. For example, the components of the vertebral pedicle screw system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral pedicle screw system may be formed or constructed material composites, including the above materials, to achieve various desired characteristics such as strength, rigidity, elasticity, compliance, biomechanical performance, durability and radiolucency or imaging preference. The components of the present vertebral pedicle screw system, individually or collectively, may also be fabricated from a heterogeneous material such as a combination of two or more of the above-described materials. The components of the vertebral pedicle screw system may be monolithically formed, integrally connected or include fastening elements and/or instruments, as described herein. The components of the vertebral pedicle screw system may be formed using a variety of subtractive and additive manufacturing techniques, including, but not limited to machining, milling, extruding, molding, 3D-printing, sintering, coating, vapor deposition, and laser/beam melting. Furthermore, various components of the vertebral pedicle screw system may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral pedicle screw system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral pedicle screw system may be employed with surgical procedures, as described herein, and/or, for example, corpectomy, discectomy, fusion and/or fixation treatments that employ spinal implants to restore the mechanical support function of vertebrae. In some embodiments, the pedicle screw system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example).

The vertebral pedicle screw system may be employed, for example, in a distraction-based systems that may include growing rods, a compression-based system such as tether and vertebral staples and guided-growth system that allows anchors to slide over the rod as in Luque trolley and Shilla systems.

This application incorporates by reference in its entirety U.S. Published Application 2020/0022740, entitled "SET SCREW SENSOR PLACEMENT," assigned to Warsaw Orthopedic, Inc.

FIG. 1 illustrates an example anchoring assembly 10 and longitudinal member 100 according to an embodiment. As illustrated in FIG. 1, an anchoring assembly 10 includes a screw 20 and an anchoring member 30. The screw 20 has an elongated shape with a first end mounted within a vertebral member 200 and a second end extending outward above the vertebral member 200. The anchoring member 30 is configured to operatively connect to the second end of the screw 20 and is movably connected to the screw 20 to accommodate the longitudinal member 100 positioned at various angular positions. The anchoring member 30 includes a channel 31 sized to receive the longitudinal member 100. A set screw 50 attaches to the anchoring member 30 to capture the longitudinal member 100 within the channel 31.

Figure 2:
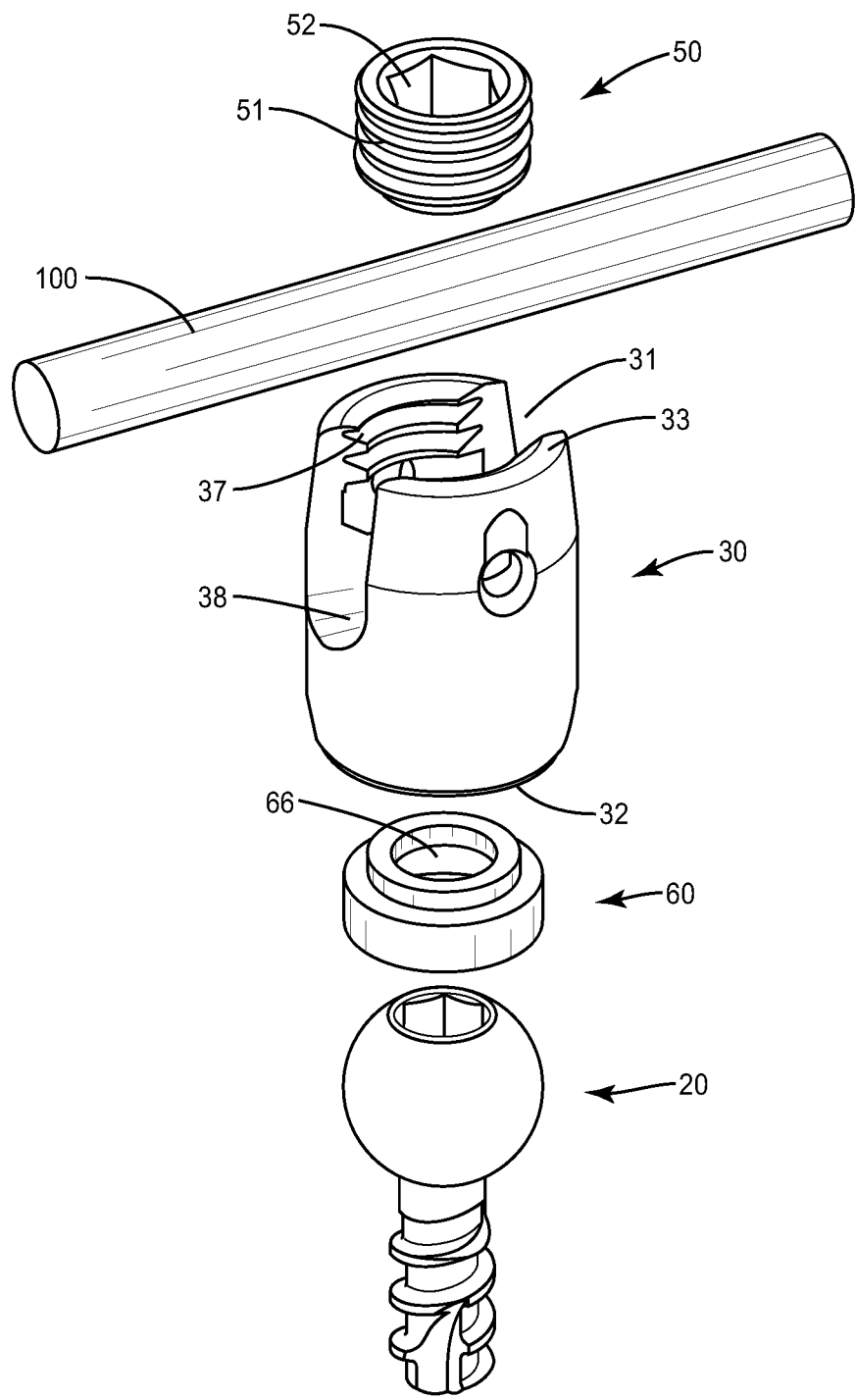
FIG. 2 illustrates an example exploded view of a screw assembly and longitudinal member according to an embodiment.

FIG. 2 illustrates an example exploded view of a screw assembly and longitudinal member according to an embodiment. As shown by FIG. 2, anchoring member 30 provides a connection between the screw 20 and longitudinal member 100. Anchoring member 30 includes a first end 32 that faces towards the vertebral member 200, and a second end 33 that faces away. A chamber is positioned between the first and second ends 32, 33 and is sized to receive at least a portion of the screw 20. In various embodiments, a first end 32 may be considered a base portion of an anchoring member 30, and a second end 33 may be considered a head portion of an anchoring member.

The second end 33 of the anchoring member 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the anchoring member 30 facing towards the channel 31. In another embodiment, the threads 37 may be on the exterior of the anchoring member 30. An interior of the anchoring member 30 may be open between the first and second ends 32, 33.

In various embodiments, an anchoring member 30 may include a washer 60. A washer 60 may be generally cylindrical and may have a hole 66 there through. As illustrated by FIG. 1 a washer 60 may be positioned near a first end 32 of an anchoring member 30. A screw 20 may engage with an anchoring member 30 via positioning through the hole 66 of a washer 60. A washer 60 may include recessed portions which may be configured to accommodate placement of a longitudinal member 100 therein. The use of a washer 60 in connection with an anchoring member 30 may help minimize misalignment of the longitudinal member within the anchoring member.

Figure 13A:
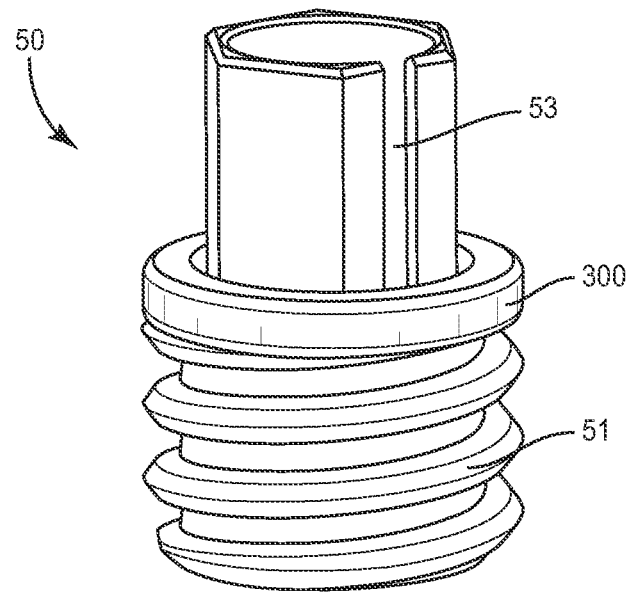
FIGS. 13A and 13B each illustrate an example set screw according to an embodiment.
Figure 13B:
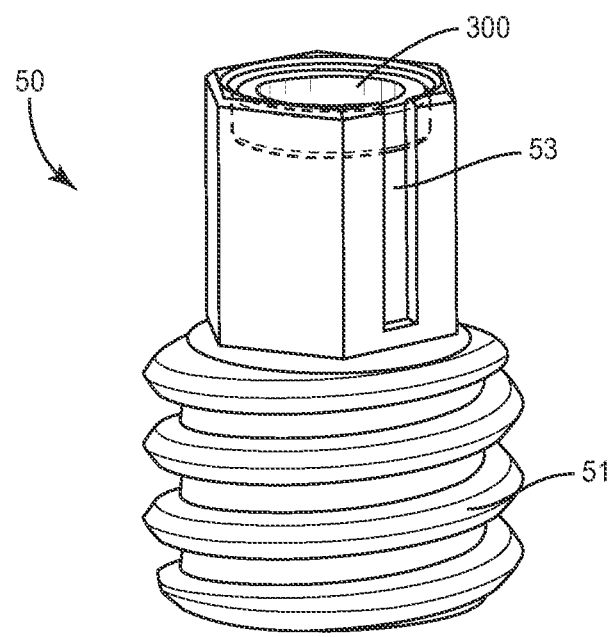

In an embodiment, set screw 50 attaches to the anchoring member 30 and captures the longitudinal member 100 within the channel 31. As illustrated in FIG. 2, the set screw 50 may be sized to fit within the interior of the channel 31 and include exterior threads 51 that engage threads 37 on the anchoring member 30. A driving feature 52 may be positioned on a top side to receive a tool during engagement with the anchoring member 30. In some embodiments, the set screw 50 may be mounted on an exterior of the anchoring member 30. Set screw 50 includes a central opening and is sized to extend around the second end 33. A set screw 50 may be a break-off set screw or a non-break-off set screw. In certain embodiments, a set screw 50 may include a slot 53 for receiving or routing of electronic connections as illustrated in FIGS. 13A and 13B. Threads 51 are positioned on an inner surface of the central opening to engage with the external threads 37 on the anchoring member 30. The set screw 50 and anchoring member 30 may be constructed for the top side of the set screw 50 to be flush with or recessed within the second end 33 when mounted with the anchoring member 30. FIG. 13A illustrates an example set screw 50 having an antenna 300 positioned on an external portion of the set screw. FIG. 13B illustrates an example set screw 50 having an antenna 300 positioned internally in a central opening of the set screw.

Figure 3:
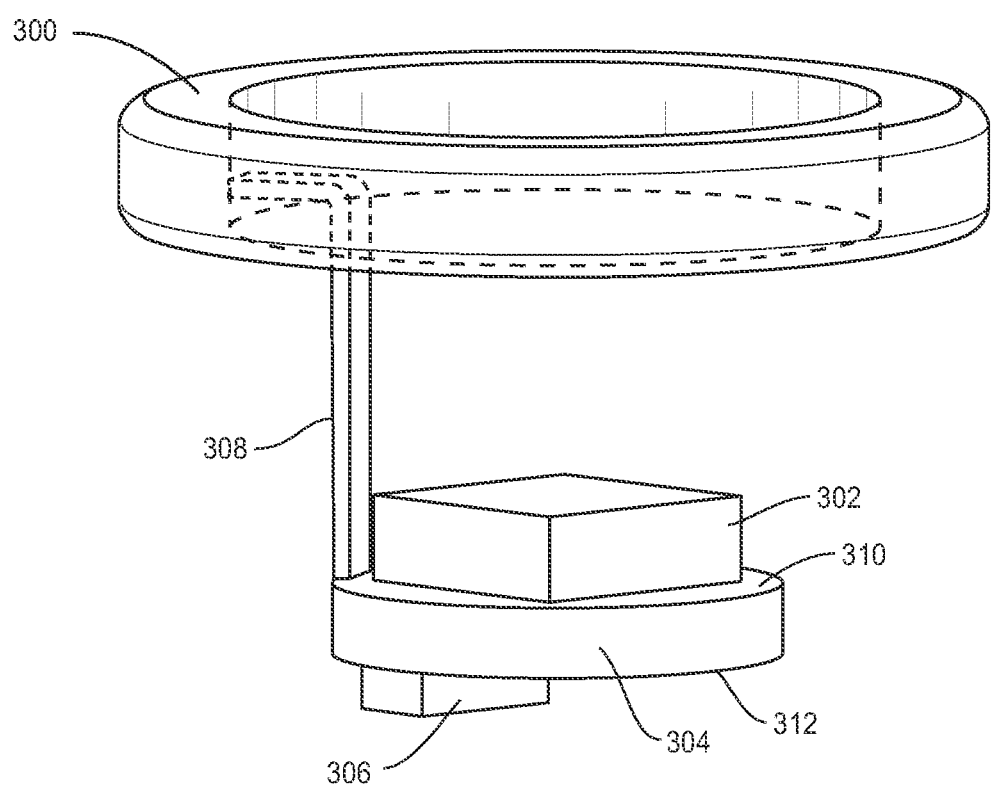
FIG. 3 illustrates an example load sensing assembly for a set screw according to an embodiment.

FIG. 3 illustrates an example load sensing assembly for a set screw according to an embodiment. As illustrated by FIG. 3, a load sensing assembly may include an antenna 300, such as a radio frequency identification (RFID) coil, a near field-communication (NFC) antenna or other short-range communication transmitter and/or receiver. A load sensing assembly may include one or more integrated circuits 302 such as, for example, an RFID chip 302 or an NFC chip. A load sensing assembly may include one or more electronics components 304 and/or a strain gauge 306, such as for example a silicon strain gauge. A strain gauge 306 may be a device that measures strain on an object. For instance, a strain gauge 306 may measure a force between a set screw and a longitudinal member when the set screw is engaged with an anchoring member. A strain gauge 306 may include one or more sensors or sensor nodes that measure strain, force, resistance, load and or the like.

In an embodiment, one or more of the electronics components 304 may include a flexible electronics component, such as, for example, a flex circuit or one or more electrical circuits. The antenna 300 may be operably connected to the electronics component 304 via a connecting member 308. For instance, as shown in FIG. 3, the connecting member 308 may be connected to both the antenna 300 and the electronics component 304. The connecting member 308 may be positioned perpendicularly to both the antenna 300 and the electronics component 304. In various embodiments, a connecting member 308 and an antenna 300 and/or electronics component 304 may be constructed integrally or may be separately constructed and attached together in any suitable manner, such as for example by adhesive, chemical, mechanical or cement bonding.

The integrated circuit 302 may be operably connected to the electronics component 304. For instance, as illustrated in FIG. 3, an electronics component 304 may have a top surface 310 and a bottom surface 312. An integrated circuit 302 may be positioned on the top surface 310 of an electronics component 304, and may be connected to the top surface in any suitable manner, including, for example, adhesive, chemical, mechanical or cement bonding. An integrated circuit 302 may include memory according to an embodiment. The memory may be used to store various information. For example, one or more measurements of a strain gauge 306 may be stored in memory. As another example, a unique identifier associated with a load sensing assembly, a component thereof, or a set screw may be stored in memory. Additional and/or alternate information or types of information may be stored according to this disclosure.

A strain gauge 306 may be operably connected, for example by adhesive, cement, mechanical or chemical bonding, to the electronics component 304. For instance, a strain gauge 306 may be operably connected to the electronics component 304 via the bottom surface 312 of the electronics component 304. A strain gauge 306 may be connected to the bottom surface 312 of an electronics component 304 in any suitable manner including, without limitation, via an adhesive bonding agent.

As shown in FIG. 3, an antenna 300 may have a generally curved shape. The antenna 300 may include a first end and a second end. The antenna 300 may include an opening that extends from the first end toward the second end.

Figure 4A:
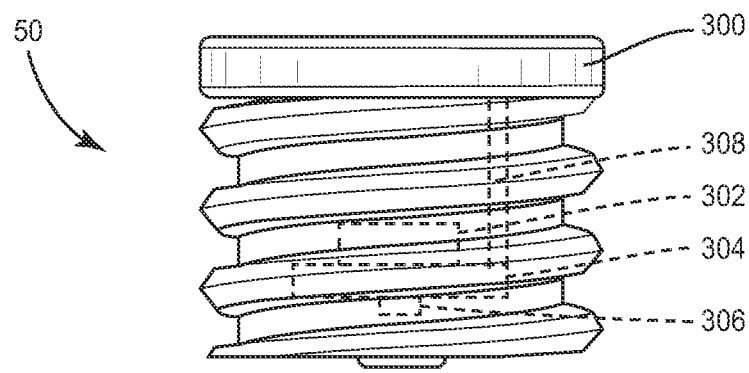
FIGS. 4A and 4B illustrates a load sensing assembly mounted to a set screw according to an embodiment.
Figure 4B:
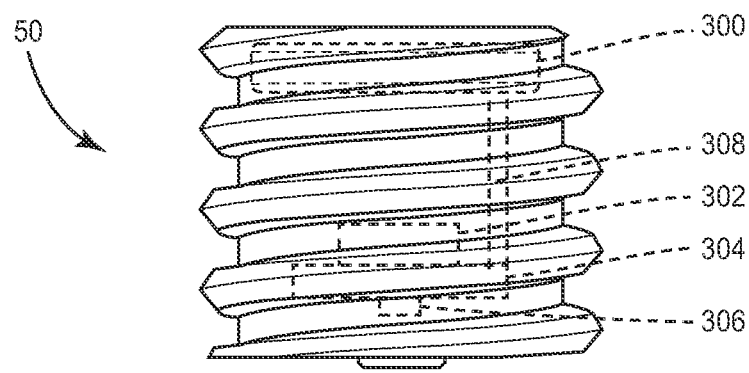

As illustrated in FIG. 4A, a load sensing assembly may be configured to be mounted to a set screw. The antenna 300 is sized to extend around the set screw such that the integrated circuit 302, electronics component 304, strain gauge 306 and connecting member 308 are positioned within the central opening of the set screw as illustrated in FIG. 4A. As illustrated in FIG. 4A, the antenna 300 may circumferentially surround at least a portion of the exterior of the set screw. In other embodiments, as illustrated by FIG. 4B, the antenna 300 may be positioned at least partially inside of the central opening of a set screw.

Figure 5:
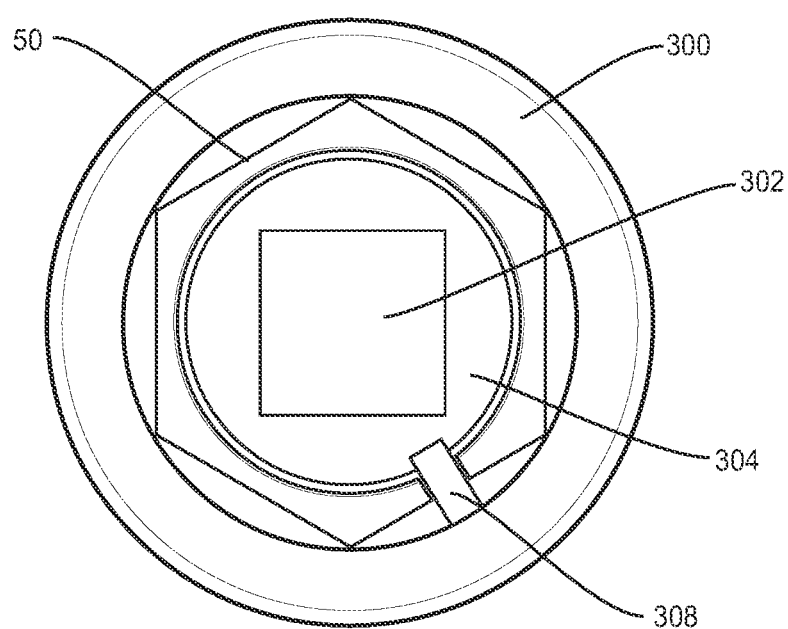
FIG. 5 illustrates a top view of a load sensing assembly mounted to a set screw according to an embodiment.

In certain embodiments, the strain gauge 306 may be connected to a portion of the central opening of the set screw in any suitable manner including, without limitation via an adhesive. The strain gauge 306 may be connected to a portion of the central opening such that it is positioned to measure a force between the set screw and a longitudinal rod when the set screw engages with an anchoring member. FIG. 5 illustrates a top view of a load sensing assembly mounted to a set screw according to an embodiment.

Figure 6:
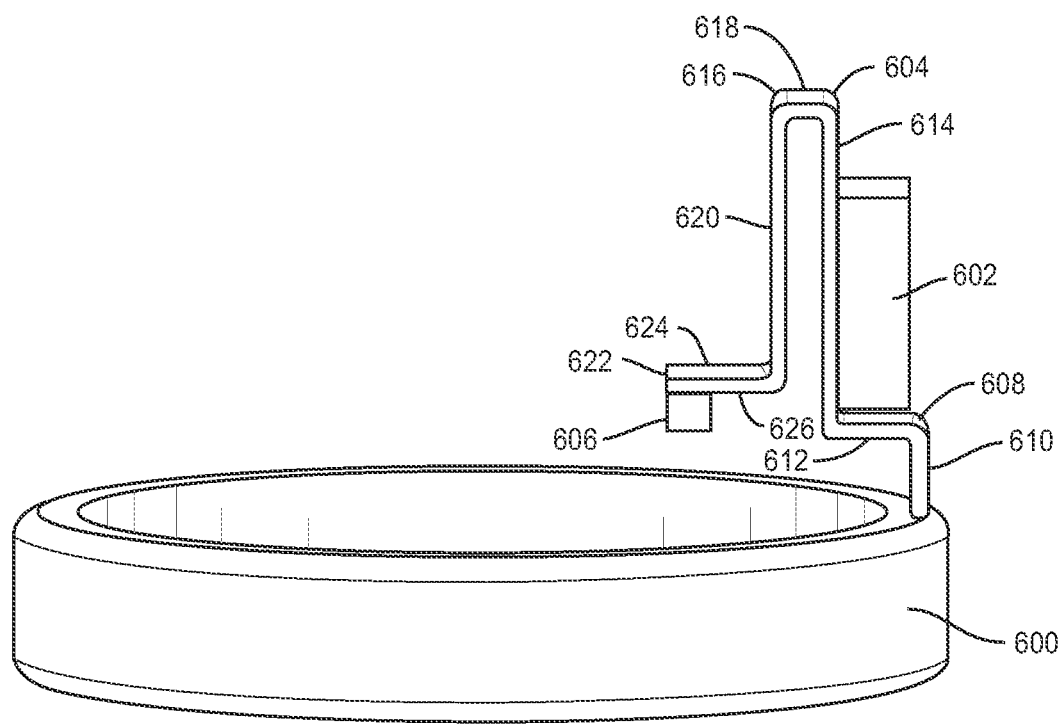
FIG. 6 illustrates an example load sensing assembly according to an embodiment.

FIG. 6 illustrates an example load sensing assembly according to an embodiment. The load sensing assembly illustrated in FIG. 6 may be mounted to an anchoring member according to various embodiments. Example anchoring members may include, without limitation screws, hooks, offset connectors, cross connectors, or other types of anchors or implants. As illustrated in FIG. 6, a load sensing assembly for an anchoring member may include an antenna 600, such as a RFID coil, an NFC antenna or other short-range communication transmitter and/or receiver. A load sensing assembly may include an integrated circuit 602, one or more electronics components 604 and/or a strain gauge 606. In an embodiment, one or more of the electronics components 604 may include a flexible electronics component, such as, for example, a flexible circuit or one or more electrical circuits.

The electronics component 604 may be connected to the antenna 600 via a connecting member 608. As shown in FIG. 6, a connecting member 608 may position an electronics component perpendicularly to the antenna 600. A connecting member 608 may include a first portion 610 that attaches to an antenna 600 and extends substantially vertically and perpendicularly from the antenna. The connecting member 608 may include a second portion 612 connected to the first portion and the electronics component. The second portion 612 may extend substantially horizontally and perpendicularly to the first portion 610. The electronics component 604 may be positioned substantially perpendicularly to the second portion 612. A connecting member 608 may be constructed integrally with an antenna 600 and/or electronics component 604, or may be separately constructed and attached together in any suitable manner.

In various embodiments, the integrated circuit 602 may be connected to a first surface 614 of the electronics component 604 as illustrated in FIG. 6. The RFID chip 602 may be connected to a first surface 614 of an electronics component in any suitable manner. An integrated circuit 602 may include memory according to an embodiment. The memory may be used to store various information. For example, one or more measurements of a strain gauge 606 may be stored in memory. As another example, a unique identifier associated with a load sensing assembly, a component thereof, or an anchoring member may be stored in memory. Additional and/or alternate information or types of information may be stored according to this disclosure.

A strain gauge 606 may be connected to an electronics component 604 via a second connecting member 616. As illustrated in FIG. 6, a second connecting member 616 may include a first portion 618, a second portion 620 and a third portion 622. The first portion 618 may connect to the electronics component 604 and may extend substantially perpendicularly to the electronics component. The second portion 620 of the second connecting member 616 may be connected to the first portion 618 of the second connecting member and may extend substantially perpendicular thereto. The third portion 622 of the second connecting member 616 may be connected to the second portion 620 of the second connecting member, and may extend substantially perpendicular to the second portion.

Figure 7:
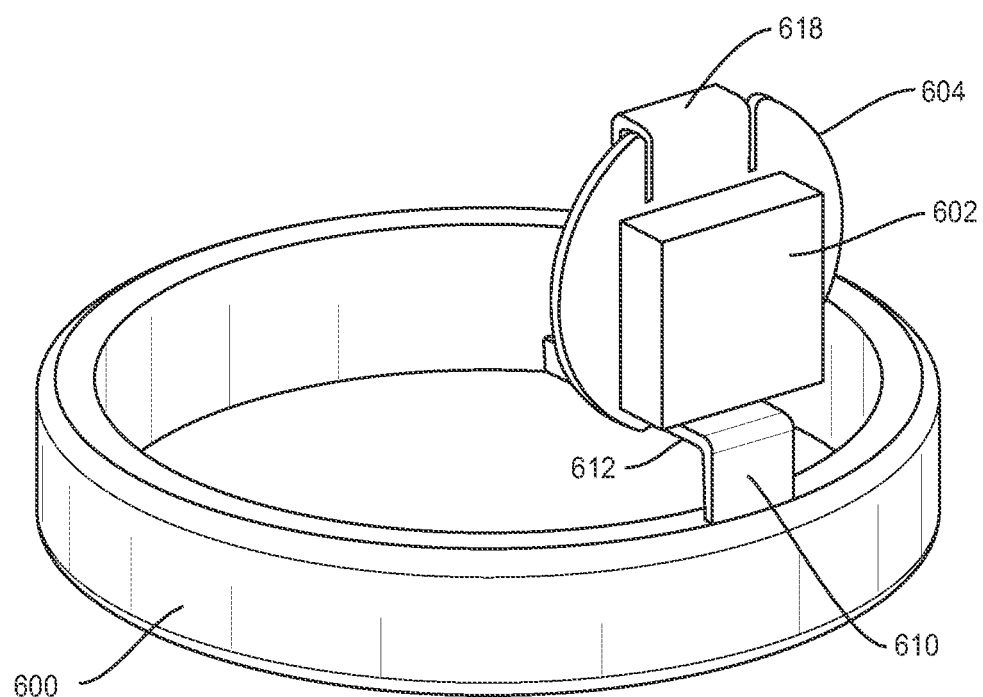
FIG. 7 illustrates a different perspective of a load sensing assembly for an anchoring member according to an embodiment.

The third portion 622 of the second connecting member 616 may have a top surface 624 and a bottom surface 626. A strain gauge 606 may be connected to the bottom surface 626 in any suitable manner. The strain gauge 606 may be configured to measure a force between the set screw and a longitudinal member. FIG. 7 illustrates a different perspective of a load sensing assembly for an anchoring member according to an embodiment.

Figure 8:
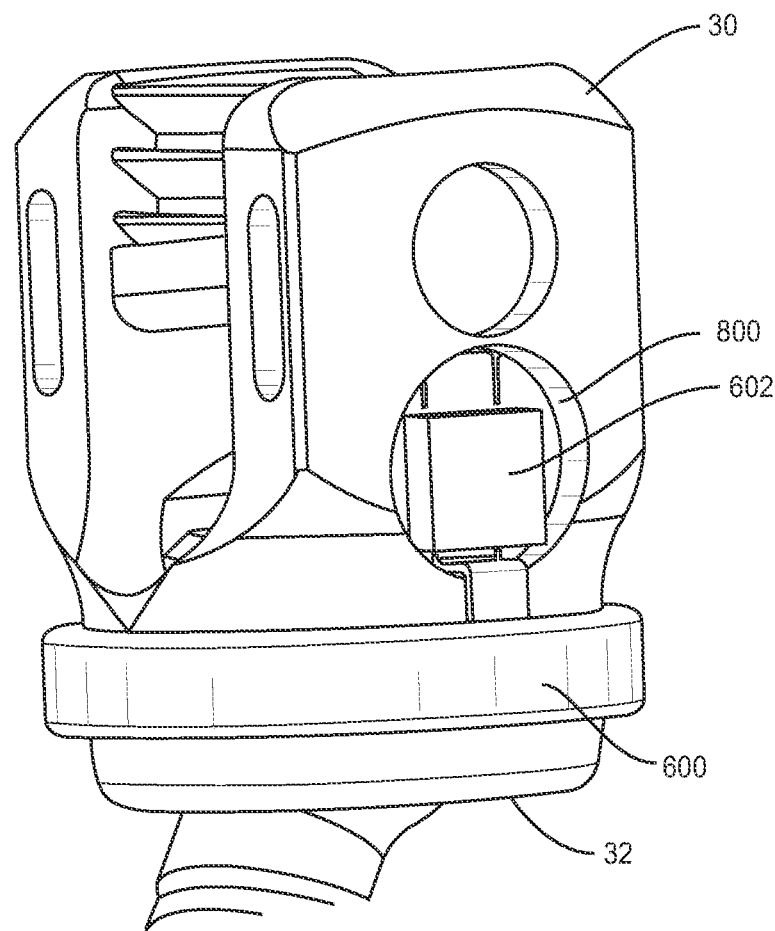
FIG. 8 illustrates a load sensing assembly connected to an anchoring member according to an embodiment.

As illustrated in FIG. 8, a load sensing assembly may be connected to an anchoring member 30. For example, a load sensing assembly may be connected to an anchoring member near a first end 32 of the anchoring member. The antenna 600 is sized to extend around the anchoring member 30, for example, near the first end 32. In various embodiments, an antenna 600 may be securely fitted around a portion of the anchoring member 30. In other embodiments, an antenna 600 may be secured to the anchoring member in any other suitable manner.

Figure 14:
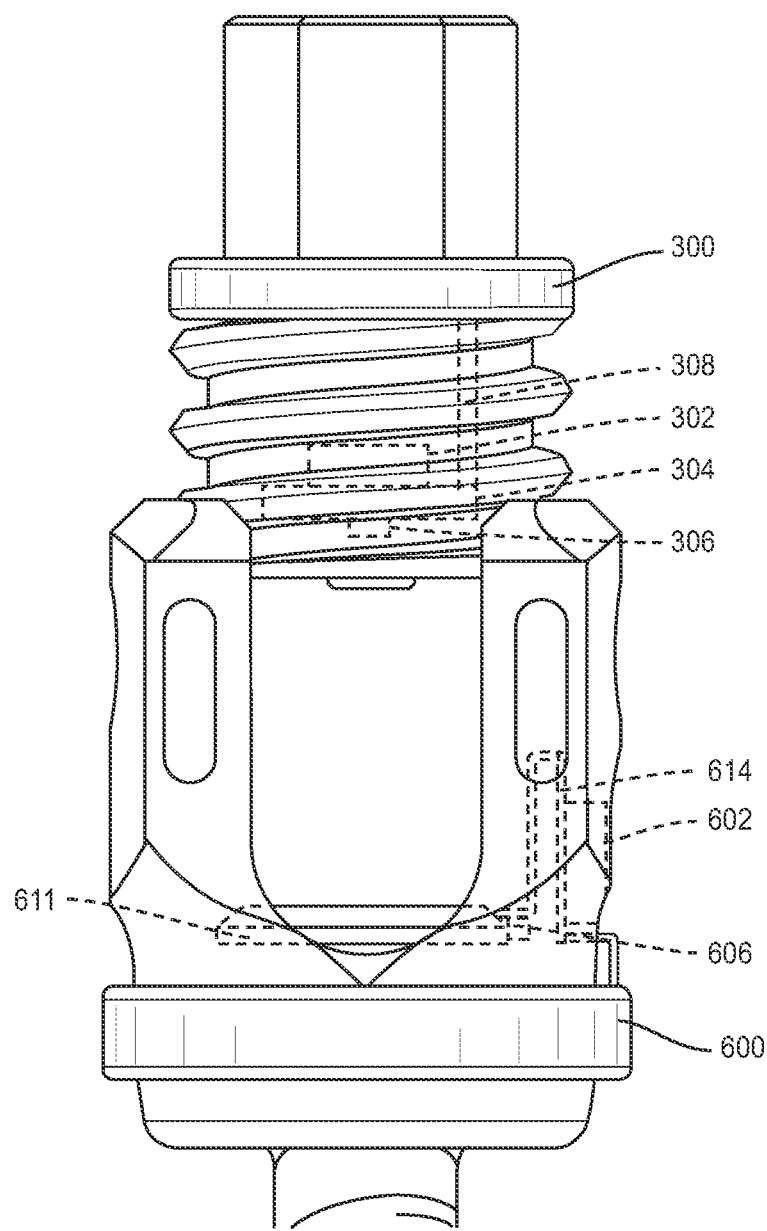
FIG. 14 illustrates an example anchoring member according to an embodiment.

The antenna 600 may be positioned on the anchoring member 30 such that the integrated circuit 602 and electronics component 604 are positioned within an opening of the anchoring member 30. For instance, as illustrated by FIG. 8, an anchoring member 30 may have one or more openings 800 that extend from an outer portion of the anchoring member into the channel 31 of the anchoring member. As illustrated by FIG. 8, the second portion of the first connecting member may extend into the opening 800 and may position the integrated circuit and/or the electronics component within the opening and/or the channel 31. Such a positioning may result in the strain gauge 606 being positioned in the channel 31 at a location where it is possible to measure a force of a longitudinal member in the channel. In an alternate embodiment, a strain gauge 606 may be positioned on or attached to a washer or pressure ring 611 within an anchoring member as illustrated by FIG. 14. In yet another embodiment, in situations where an anchoring member includes a hook member, a strain gauge 606 may be positioned on or attached to a hook portion of the hook member. Measurements obtained by the strain gauge 606 may be used to determine whether a longitudinal member is properly seated and/or torqued during and/or after implant.

Figure 9:
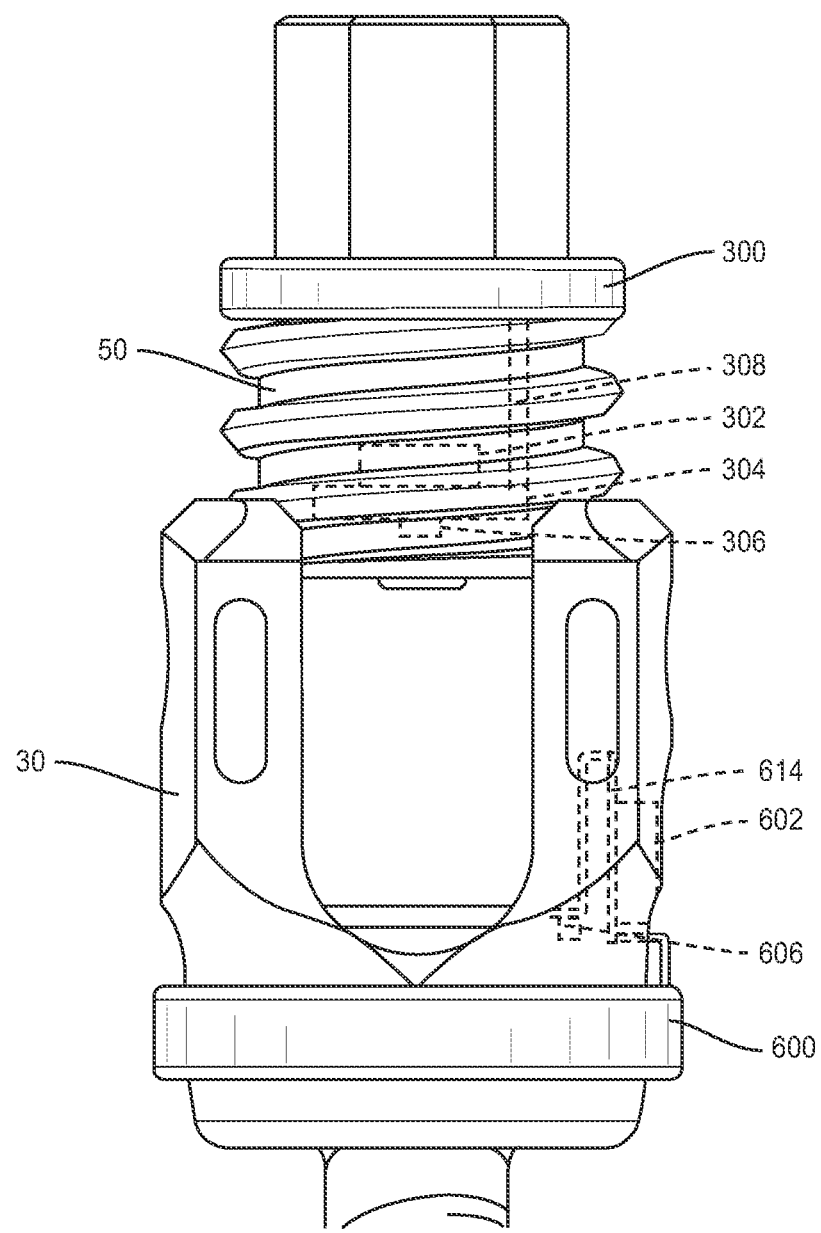
FIG. 9 illustrates a screw assembly set screw having a load sensing assembly and connected to an anchoring member that also has a load sensing assembly mounted to it according to an embodiment.
Figure 10:
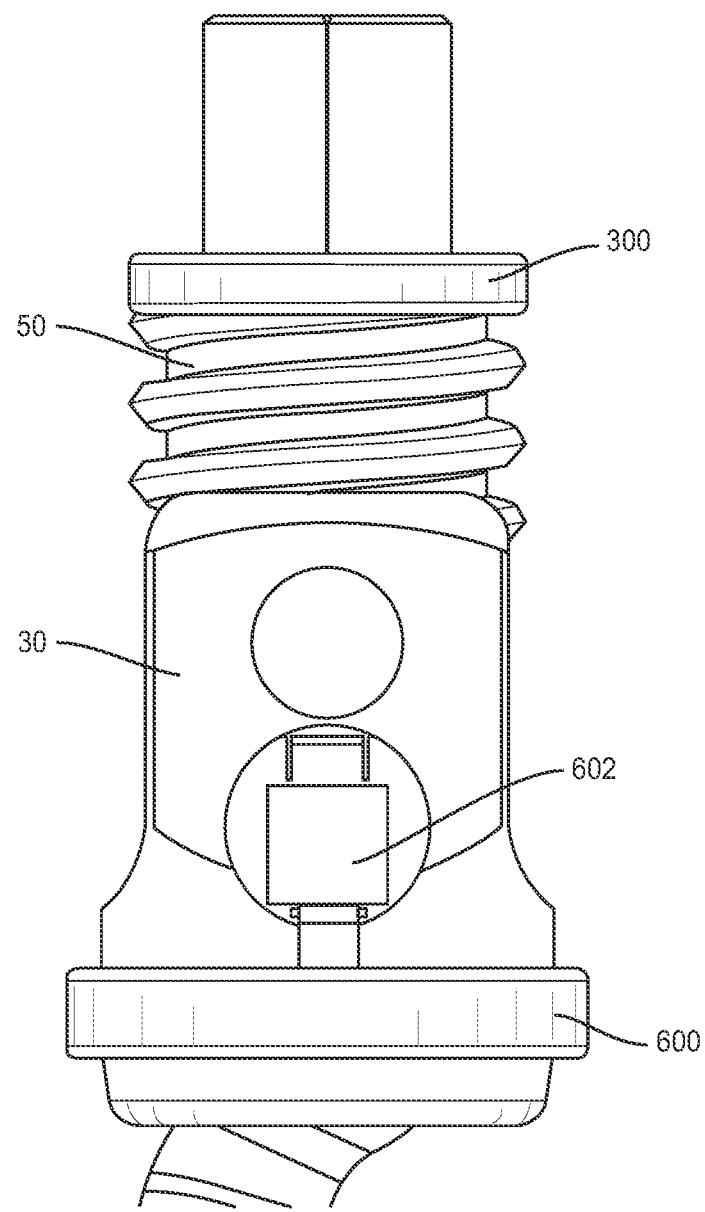
FIG. 10 illustrates a side view of the screw assembly shown in FIG. 9 according to an embodiment.
Figure 11:
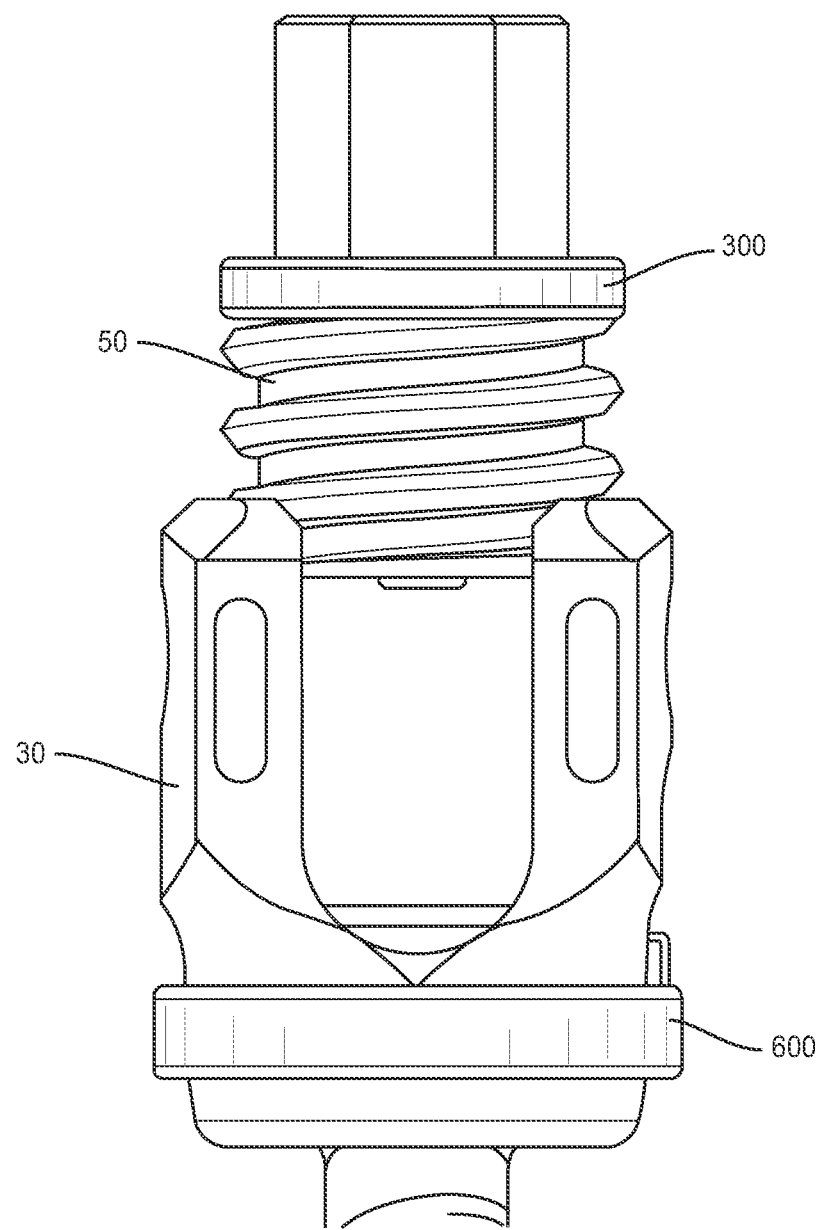
FIG. 11 illustrates a non-transparent view of the screw assembly shown in FIG. 9 according to an embodiment.

In various embodiments, a set screw having a load sensing assembly may be used with in connection with an anchoring member with or without a load, sensing assembly. FIG. 9 illustrates a set screw having a load sensing assembly engaged with an anchoring member that also has a load sensing assembly according to an embodiment. So that components of each can be clearly depicted, a longitudinal member is not shown in FIG. 9. FIG. 10 illustrates a side view of the screw assembly shown in FIG. 9 according to an embodiment. FIG. 11 illustrates a non-transparent view of the screw assembly shown in FIG. 9 according to an embodiment. Although FIGS. 9-11 illustrate an antenna located externally to a set screw, it is understood that the antenna may alternatively be located within at least a portion of the central opening of the set screw.

Figure 12:
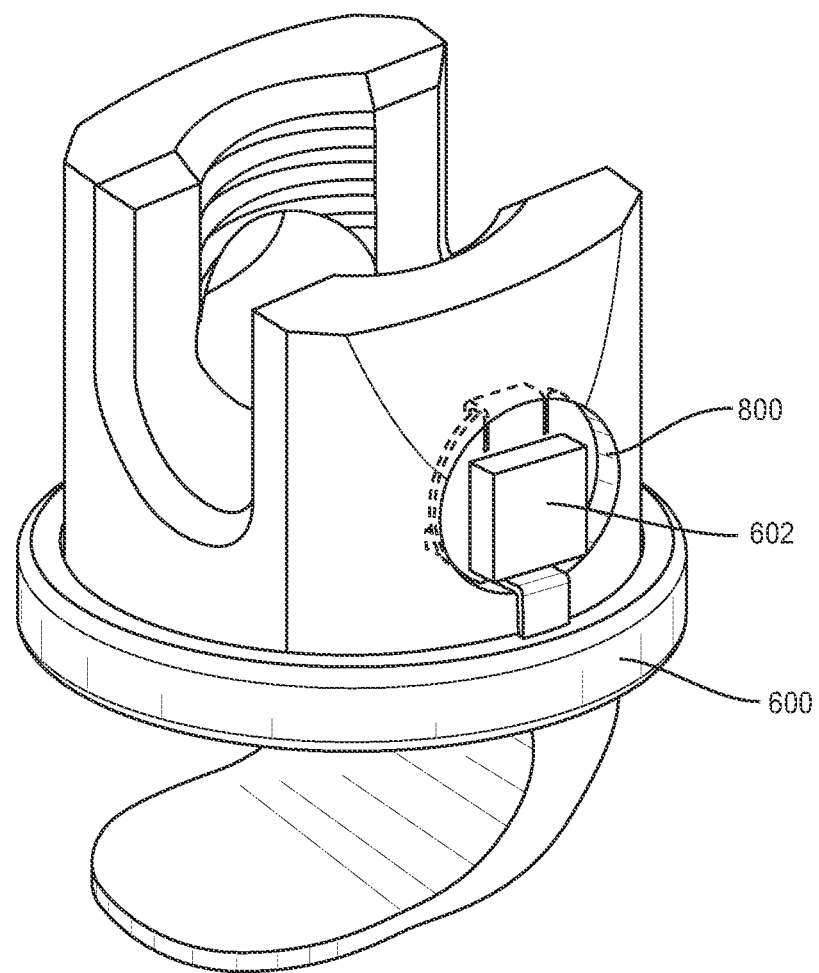
FIG. 12 illustrates an example hook member having a load sensing assembly according to an embodiment.

FIGS. 1-11 illustrate a multi-axial tulip-head pedicle screw according to various embodiments. However, it is understood that other types of anchoring members may be used within the scope of this disclosure. For example, fixed head screws or screws having differently shaped heads may be used. As another example, a hook member, a cross-link connector, an offset connector, or a hybrid hook-screw member may be used as well. FIG. 12 illustrates an example hook member having a load sensing assembly according to an embodiment.

In various embodiments, one or more measurements obtained by a strain gauge may be stored by an integrated circuit of a corresponding load sensing assembly such as, for example, in its memory. The integrated circuit may be interrogated by a reader. For instance, an RFID chip may be read by an RFID reader. As another example, an NFC chip may be read by or may otherwise communicate with an NFC reader or other NFC-enabled device. A reader may interrogate an integrated circuit when in a certain proximity to the integrated circuit. In certain embodiments, a reader may interrogate an integrated circuit that has been implanted into a patient as part of a set screw or anchoring member assembly. In other embodiments, an integrated circuit may communicate with a reader or other electronic device without being interrogated.

An integrated circuit may transmit one or more measurements to the reader. This transmission may occur in response to being interrogated by the reader, or the transmission may be initiated by the integrated circuit. The reader may receive the transmitted measurements, and may cause at least a portion of the measurements to be displayed to a user. For instance, a physician may use a reader to interrogate an RFID chip of a patient's implant. The reader may include a display, or may be in communication with a display device, which may display at least a portion of the measurements received from the RFID chip.

An integrated circuit may be passive, meaning that the chip has no internal power source and is powered by the energy transmitted from a reader. With respect to an assembly having a passive integrated circuit, the integrated circuit may not transmit information until interrogated by a reader.

In another embodiment, an integrated circuit may be active, meaning that the chip is battery-powered and capable of broadcasting its own signal. An active integrated circuit may transmit information in response to be interrogated by a reader, but also on its own without being interrogated. For instance, an active integrated circuit may broadcast a signal that contains certain information such as, for example, one or more measurements gathered by an associated strain gauge. An active integrated circuit may continuously broadcast a signal, or it may periodically broadcast a signal. Power may come from any number of sources, including, for example, thin film batteries with or without encapsulation or piezo electronics.

In various embodiments, one or more sensors may transmit information by directly modulating a reflected signal, such as an RF signal. The strain gauge sensors may form a Wireless Passive Sensor Network (WPSN), which may utilize modulated backscattering (MB) as a communication technique. External power sources, such as, for example, an RF reader or other reader, may supply a WPSN with energy. The sensor(s) of the WPSN may transmit data by modulating the incident signal from a power source by switching its antenna impedance.

One or more measurements received from a load sensing assembly may be used to make determinations of the condition of a spinal implant and/or treatment of a spinal disorder. For instance, proper placement of a longitudinal member, set screw and/or anchoring member may result in an acceptable range of force measurements collected by a strain gauge of a load sensing assembly. Measurements outside of this range may indicate a problem with the placement or positioning of a longitudinal member, set screw and/or anchoring member such as, for example, loosening of a set screw and/or anchoring member, longitudinal member failure, construct failure, yield or fracture/breakage, improper torque, breakage of the bone segment or portion, the occurrence of fusion or amount of fusion, and/or the like.

One or more tools or instruments may include a reader which may be used to gather information from one or more integrated circuit during or in connection with a procedure. For instance, a torque tool may be used to loosen or tighten a set screw. A torque tool may include a reader, or may be in communication with a reader, such that a user of the torque tool is able to obtain, in substantially real time, one or more measurements relating to the set screw and longitudinal rod placement that are measured by a strain gauge of a load sensing assembly of the set screw via the tool. For instance, as a user is applying torque to a set screw, the user may see one or more force measurements between the set screw and the longitudinal member in order to determine that the positioning of the set screw and/or longitudinal member is correct and that the proper force is being maintained. In certain embodiments, a tool or instrument may include a display device on which one or more measurements may be displayed. In other embodiments, a tool or instrument may be in communication with a display device, and may transmit one or more measurements for display on the display device via a communications network.

In some embodiments, an electronic device, such as a reader or an electronic device in communication with a reader, may compare one or more measurements obtained from an integrated circuit to one or more acceptable value ranges. If one or more of the measurements are outside of an applicable value range, the electronic device may cause a notification to be made. For instance, an electronic device may generate an alert for a user, and cause the alert to be displayed to the user via a display device. Alternatively, an electronic device may send an alert to a user such as via an email message, a text message or otherwise.

An integrated circuit of a load sensing assembly may store a unique identifier associated with the component to which the load sensing assembly corresponds. For instance, an integrated circuit of a load sensing assembly for a set screw may store a unique identifier associated with the set screw. Similarly, an integrated circuit of a load sensing assembly for an anchoring member may store a unique identifier associated with the anchoring member. The integrated circuit may transmit the unique identifier to an electronic device. For instance, when a reader interrogates an integrated circuit, the integrated circuit may transmit a unique identifier for a component that is stored by the integrated circuit to the reader.

Having access to a unique identifier for a component may help a user ascertain whether the measurements that are being obtained are associated with the component of interest. Also, having access to a unique identifier for a component may help a user take inventory of one or more components. For instance, after spinal surgery, a physician or other health care professional may use a reader to confirm that all of the set screws and anchoring members allocated for the procedure have been used and are positioned in a patient.

Figure 15A:
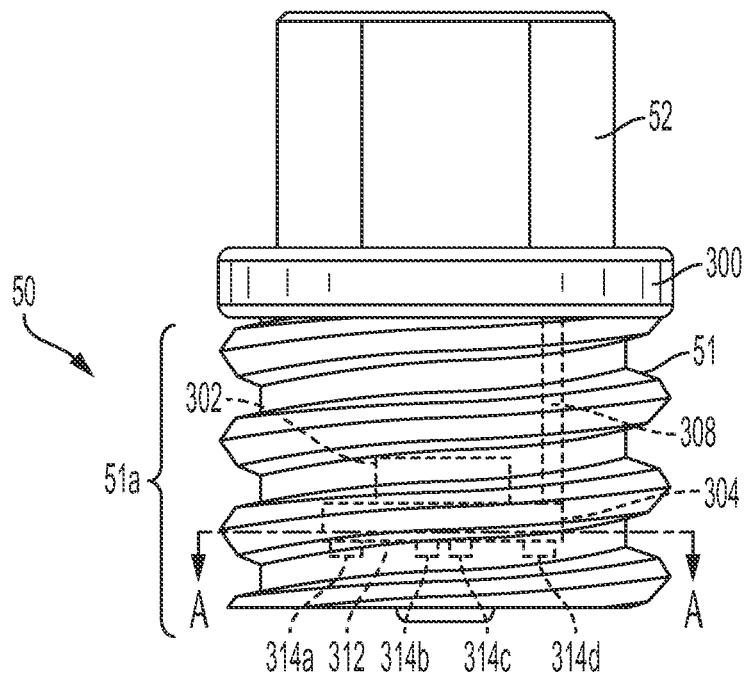
FIG. 15A illustrates a side view of a load sensing assembly mounted to a set screw according to an embodiment.
Figure 15B:
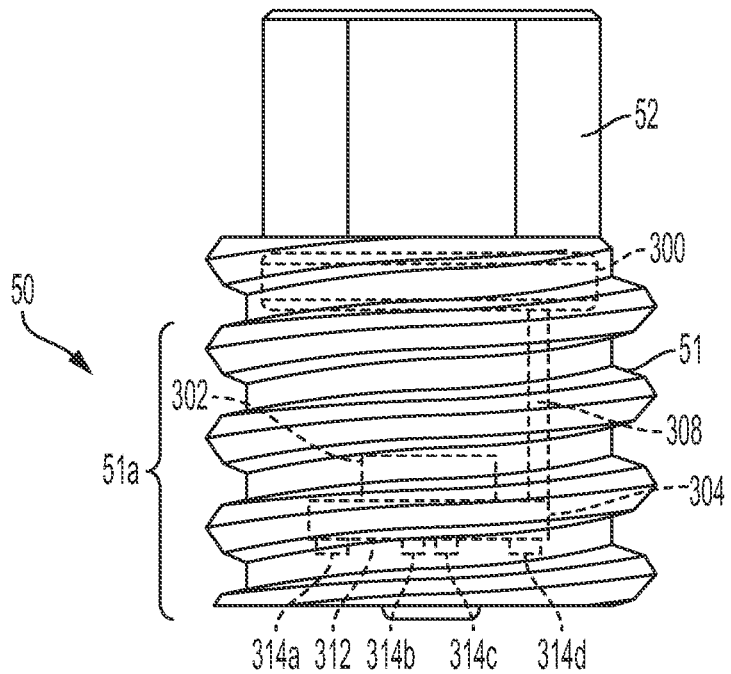
FIG. 15B illustrates a side view of a load sensing assembly mounted to a set screw according to an embodiment.

FIG. 15A illustrates a side view of a load sensing assembly mounted to the set screw 50 according to an embodiment. FIG. 15B illustrates a side view of a load sensing assembly mounted to the set screw 50 according to an embodiment. FIGS. 15C-15E illustrate bottom views taken at cross-section A-A in FIG. 15A of sensors positioned on the load sensing assembly according to an embodiment.

In one or more embodiments, the set screw 50, external threads 51, driving feature 52, antenna 300, integrated circuit 302, electronics component 304, and connecting member 308 include one or more of the same features discussed above with respect to the load sensing assembly mounted to the set screw 50 as described in FIGS. 3 through 5. Accordingly, a description of these same features is not repeated.

In one or more cases, the driving feature 52 of the set screw 50 may be positioned on top of the proximal end of the external threads 51. The driving feature 57 is configured to receive a tool, such as a screw driver, during engagement with the anchoring member 30. The driving feature 52 may include a bore 59 that extends from an outer top surface of the break-off head 58 and into a portion of the threaded portion 51a of the set screw 50. In one or more cases, the bore 59 may have a cylindrically shaped opening when view from a top surface of the set screw 50a. In one or more other cases, the bore 59 may have a star shaped opening, e.g., a shape to receive a hexalobe screw driver, with an inner cylindrically shaped opening when viewed from a top surface of the set screw 50a. The bore 59 may provide a working area for placing one or more sensors, such as sensors 314a, 314b, 314c, and 314d within the set screw 50. For the cases in which the bore 59 has a star shaped opening with an inner cylindrically shaped opening, the working area of the inner cylindrically shaped opening may be 2 to 5 mm in diameter, and more preferably at or about 3.65 mm in diameter. For the cases in which the bore 59 has a cylindrically shaped opening, the working area for the cylindrically shaped opening may be 3 to 7 mm in diameter, and more preferably at or about 5.35 mm in diameter. For the cases in which strain gauges are used as sensors 314a, 314b, 314c, and 314d in the driving feature 52 having the cylindrically shaped bore 59, the strain gauges may experience higher strain values than a driving feature 52 having the star shaped opening with an inner cylindrically shaped bore 59.

The driving feature 52 may have an external shape configured to engage with a tool, such as a screw driver, to rotate the set screw 50. The driving feature 52 may be configured in an external shape to enable a positive, non-slip engagement of the driving feature 52 by the tool. For example, in one or more cases, the outer perimeter of the driving feature 52 may be configured in a hexagonal shape. In one or more other cases for example, the outer perimeter, that is, the outer surface, of the driving feature 52 may be configured in a square shape, pentagonal shape, star shape, or the like. The driving feature 52 may include a slot, similar to slot 53, for receiving or routing electronic connections as illustrated in FIGS. 13A and 13B. In one or more cases, the driving feature 52 may be configured to break-off from the threaded portion 51a. In one or more other cases, the driving feature 52 may configured to not break-off from the threaded portion 51a.

In one or more cases, the antenna 300, connecting member 308, integrated circuit 302, and the electronics component 304 may be arranged in a similar manner and configured to operate in a similar manner as discussed with respect to FIGS. 3 and 4B. In one or more cases, the antenna 300 is configured to transmit signals from at least one of the integrated circuit 302, the electronics component 304, and sensors 314a, 314b, 314c, and 314d to a reader. In one or more cases, the antenna 300 is configured to receive signals from the reader. For example, the antenna 300 may receive an ON signal from reader, in which the ON signal powers on the load sensing assembly. In one or more cases, the antenna 300 may be sized to fit around a portion of the driving feature 52, as shown in FIG. 15A, and/or at least a portion of the exterior of the set screw 50, as shown in FIG. 4A. In one or more other cases, the antenna 300 may be sized to fit within a portion of the bore 59 of the threaded portion 51a, as shown in FIG. 15B, and/or within a portion of the central opening of the set screw 50, as shown in FIG. 4B. In one or more cases, the antenna 300 includes a ferrite core configured to amplify the transmission signals of the antenna 300.

In one or more cases, the sensors 314a, 314b, 314c, and 314d may be connected to a portion of the bore 59 of the set screw 50 in any suitable manner including, without limitation via an adhesive. The sensors 314a, 314b, 314c, and 314d may be strain gauges, impedance sensors, pressure sensors, capacitive sensors, temperature sensors, or the like. The sensors 314a, 314b, 314c, and 314d may be connected to a portion of the bore 59, i.e., the central opening. For the cases in which the sensors 314a, 314b, 314c, and 314d are strain gauges, the sensors 314a, 314b, 314c, and 314d may be positioned to measure a force between the set screw 50 and the longitudinal member 100 when the set screw 50 engages with the anchoring member 30, e.g., a nominal clamping force. The sensors 314a, 314b, 314c, and 314d may be operably connected to a bottom surface 312 of the electronics component 304. The sensors 314a, 314b, 314c, and 314d may directly interface with the set screw 50 and the electronics component 304. For the cases in which the sensors 314a, 314b, 314c, and 314d are temperature sensors, the sensors 314a, 314b, 314c, and 314d may be positioned above the integrated circuit 302. For the cases in which the sensors 314a, 314b, 314c, and 314d are capacitive sensors may be connected to a portion of the bore 59. In one or more cases, the set screw 50 may include all of the same type of sensors, for example, the set screw 50 may include all strain gauges. In one or more other cases, the set screw 50 may include a mix of sensors, for example, the set screw 50 may include strain gauges and temperature sensors.

FIGS. 15C-15E illustrate bottom views taken at cross-section A-A in FIG. 15A of sensors positioned on the load sensing assembly according to an embodiment. It should be noted that FIGS. 15C-15E illustrate embodiments that utilize four sensors, such as sensors 314a, 314b, 314c, and 314d; however, it should be understood that embodiments are contemplated that use more than 4 sensors and that use less than 4 sensors.

In one or more cases, the sensors 314a, 314b, 314c, and 314d may be linearly arranged across the electronics component 304, as shown in FIG. 15C. That is, the sensors 314a, 314b, 314c, and 314d may be linearly arranged across the bore 59, i.e., the central opening, of the set screw 50. The sensors 314a, 314b, 314c, and 314d may directly interface with the set screw 50 and the electronics component 304. In one or more cases in which the sensors are linearly arranged, two sensors, such as sensors 314b and 314c, may be arranged in close proximity to one another over a central portion 304a of the electronics component 304, and two other sensors, such as sensors 314a and 314d, may be each arranged on opposite sides from one another on an outer portion 304b of the electronics component 304. For example, the sensor 314a may be arranged on the outer portion 304b, e.g., a distal end, of the electronics component 304, and the sensor 314d may be arranged on the outer portion 304b, e.g., of the electronics component 304 opposite the sensor 314a. In one or more other cases in which the sensors are linearly arranged, the sensors may be linearly arranged on the electronics component 304, such that there is equal spacing between each of the sensors. In one or more cases, the two sensors 314b and 314c arranged in close proximity to one another may be active strain gauges configured to measure the greatest area of strain on the set screw 50. The two sensors 314a and 314d arranged on the outer portion 304b of the electronics component 304 may be compensating strain gauges configured to measure areas of lesser strain than those measured by sensors 314b and 314c.

The sensors 314a, 314b, 314c, and 314d are illustrated in FIG. 15C as being strain gauges having a "U" shape or substantially U-like shape. In one or more cases, the opening of the U-shaped sensor 314a and the opening of the U-shaped sensor 314d may face each other. In one or more cases, the opening of the U-shaped sensor 314b and the opening of the U-shaped sensor 314c may face away from one another. In one or more cases, the openings of the U-shaped sensors 314a and 314d may be positioned to face towards the central portion 304a of the electronics component 304 and the bore 59. In one or more cases, the openings of the U-shaped sensors 314b and 314c may be positioned to face towards the outer portion 304b of the electronics component 304 and the bore 59.

In one or more cases, the sensors 314a, 314b, 314c, and 314d may be circumferentially arranged around the electronics component 304. The sensors 314a, 314b, 314c, and 314d may be circumferentially arranged around the outer portion 304b of the electronics component 304, as shown in FIG. 15D. That is, the sensors 314a, 314b, 314c, and 314d may be circumferentially arranged around the outer portion of the bore 59, i.e., the central opening, of the set screw 50. The sensors 314a, 314b, 314c, and 314d may directly interface with the set screw 50 and the electronics component 304. In one or more cases, the two sensors 314a and 314c may be active strain gauges arranged around the outer portion 304b of the electronics component 304 in the areas of greatest strain on the set screw 50. The two sensors 314b and 314d may be compensating strain gauges arranged on the outer portion 304b of the electronics component 304 in the areas of lesser strain than those measured by sensors 314a and 314c. For example, for the cases in which the bore 59 has a star shaped opening with an inner cylindrically shaped opening, the sensors 314a and 314c may be positioned to measure areas 309a and 309b, in which the strain of area 309a ranges from about 0.0054995 microstrain to about 0.0035 microstrain and the strain of area 309b ranges from about 0.0035 microstrain to about 0.003 microstrain. The sensors 314b and 314d may be positioned to measure areas 309c and 309d, in which the strain of area 309c ranges from about 0.003 microstrain to about 0.0025 microstrain and the strain of area 309d ranges from about 0.0025 microstrain to about 0.002 microstrain.

The sensors 314a, 314b, 314c, and 314d are illustrated in FIG. 15D as being strain gauges having a "U" shape or substantially "U"-like shape. In one or more cases, the openings of the U-shaped sensors 314c and 314d may be positioned to face away from the central portion 304a of the electronics component 304 and the bore 59 and towards the outer portion 304b. In one or more cases, the opening of the U-shaped sensor 314b may be positioned to face, following an arc-like path from the sensor 314b to the sensor 314a, a rear surface of the U-shaped sensor 314a. In one or more cases, the opening of the U-shaped sensor 314a may be positioned to face, following an arc-like path from the sensor 314a to the sensor 314d, a side surface of the U-shaped sensor 314a. The openings of the U-shaped sensors 314a and 314d may be positioned to face in the same direction. The openings of the U-shaped sensors 314b and 314c may be positioned to face in the same direction. The openings of the U-shaped sensors 314a, 314b, 314c, and 314d may be positioned to face towards the outer portion 304b of the electronics component 304 and the bore 59.

In one or more cases, a portion of the sensors may be arranged on the central portion 304a of the electronics component 304, and another portion of the sensors may be arranged on the outer portion 304b of the electronics component 304. For example, sensors 314a and 314b may be arranged on the central portion 304a of the electronics component 304, and sensors 314d and 314c may be arranged on the outer portion 304b of the electronics component 304, as shown in FIG. 15E. In one or more cases, the two sensors 314a and 314b arranged on the central portion 304a of the electronics component 304 may be active strain gauges configured to measure the greatest area of strain on the set screw 50. The two sensors 314d and 314c arranged on the outer portion 304b of the electronics component 304 may be compensating strain gauges configured to measure areas of lesser strain than those measured by sensors 314a and 314b. For example, for the cases in which the bore 59 has a cylindrically shaped opening, the sensor 314b may be positioned to measure areas 311a, 311b, and 311c, in which the strain of area 311a ranges from about 0.009 microstrain to about 0.008 microstrain, the strain of area 311b ranges from about 0.008 microstrain to about 0.007 microstrain, and the strain of area 311c ranges from about 0.007 microstrain to about 0.006 microstrain. The sensor 314a may be positioned to measure areas 311c and 311d, in which the strain of area 311b ranges from about 0.006 microstrain to about 0.005 microstrain. The sensor 314d may be positioned to measure areas 311e and 311f, in which the strain of area 311e ranges from about 0.005 microstrain to about 0.004 microstrain and the strain of area 311f ranges from about 0.004 microstrain to about 0.003 microstrain. The sensor 314c may be positioned to measure area 311f.

In one or more cases, using the center of the electronics component 304 as a reference point, the sensors 314c and 314d may be positioned at or about 90° from one another. In one or more cases, using the center of the electronics component 304 as a reference point, the sensors 314a and 314b may be positioned at or about 90° from one another. The sensors 314a, 314b, 314c, and 314d are illustrated in FIG. 15E as being strain gauges having a "U" shape or substantially "U"-like shape. In one or more cases, the openings of the U-shaped sensors 314c and 314d may be positioned to face away from the central portion 304a of the electronics component 304 and the bore 59 and towards the outer portion 304b. In one or more cases, the opening of the U-shaped sensor 314b may be positioned to face, following an arc-like path from the sensor 314b to the sensor 314a, a rear surface of the U-shaped sensor 314a. In one or more cases, the opening of the U-shaped sensor 314a may be positioned to face, following an arc-like path from the sensor 314a to the sensor 314d, a side surface of the U-shaped sensor 314a. The openings of the U-shaped sensors 314a and 314d may be positioned to face in the same direction. The openings of the U-shaped sensors 314b and 314c may be positioned to face in the same direction. The openings of the U-shaped sensors 314a, 314b, 314c, and 314d may be positioned to face towards the outer portion 304b of the electronics component 304 and the bore 59.

Figure 16A:
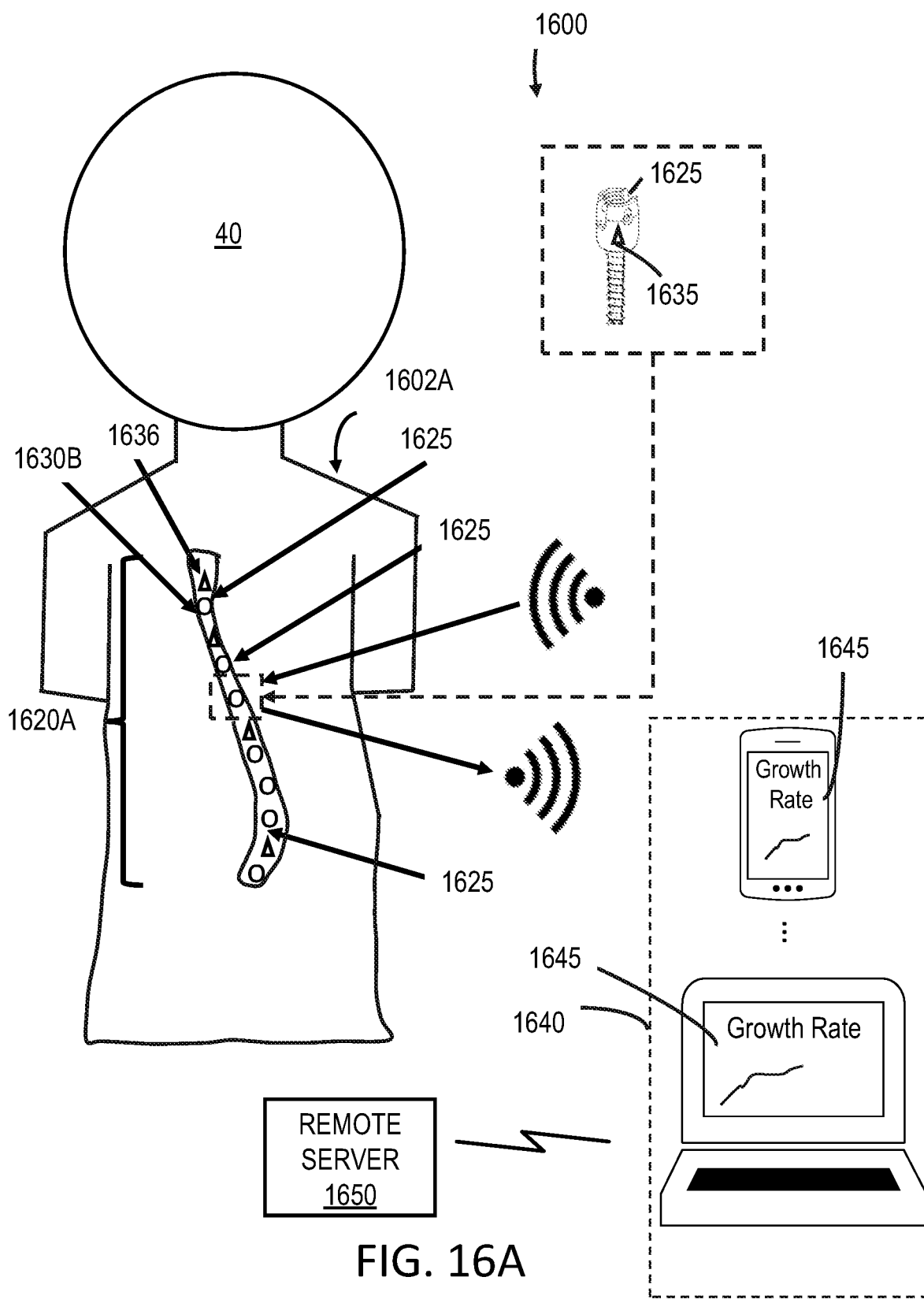
FIG. 16A illustrates an example diagram of a growth monitoring system implanted in a patient.

FIG. 16A illustrates an example diagram of a surgical implant system 1600 having a plurality of bone constructs and/or growth modulating implants having a growth monitoring (GM) system 1602 embedded in some or all of the implant bodies. The implant system 1600 may be configured to be surgically implanted in a patient 40, such as a pediatric patient. The implant system 1600 may include a bone correction system 1620A that is biocompatible for implantation into living tissue or bone. The bone correction system 1620A may be configured to treat a deformity of the bone(s) or spine using various implants, such as bone constructs 1625 and/or at least one longitudinal member device 1630A. In other embodiments, the bone correction system may be configured to correct deformity or growth of at least one bone of a limb, for example. In some embodiments, a vertebrae staple may be used. A vertebrae staple or other bone implant may modulate growth that can be measured by the electrical signals from a strain gauge embedded in the body of the implant.

The embodiments may implant in two or more bones growth modulating implants of a bone correction system 1620A. Each growth modulating implant includes an implant body having at least one sensor device embedded in the implant body. Although the embodiments illustrate vertebra bones, the load sensing assembly (FIG. 3) may be embedded in other bone constructs such as those configured to be embedded and fastened in limbs or limb bone joints. In some embodiments, the growth modulating implants may use bone constructs to fasten plates to a limb's growth plate. The lower limb bones include the femur, tibia, fibula and patella, for example. The upper limb bones include the radius, ulna and humerus, for example, The GM system 1602 may include a strain gauge 1635 (e.g., strain gauge 306) embedded in the body of a bone construct 1625 that may be positioned to measure a force or loading between the bone construct 1625 and a longitudinal member device 1630A, such as a rod. The strain gauge 1635 may include a plurality of sensors 314a, 314b, 314c, and 314d (FIGS. 15A-15E) to monitor data associated with the longitudinal growth of the bones in the spine. Alternately or in addition to, each longitudinal member device 1630A may include at least one strain gauge 1636. The strain gauge 1636 may include one or more sensors such as similar to sensors 314a, 314b, 314c, and 314d. In FIG. 16A, the strain gauges 1635 and 1636 are denoted as triangle to simplify the drawings.

The bone construct 1625 may include a load sensing assembly, as shown in FIG. 3. The GM system 1602 may include a load sensing assembly (FIG. 3) having one or more integrated circuits 302 (FIG. 3) such as, for example, an RFID chip 302 or an NFC chip, one or more electronics components 304 and/or a strain gauge 306 and antenna 300. The longitudinal member device 1630A may include a load sensing assembly similar to the load sensing assembly of FIG. 3.

The GM system 1602 may include an external monitoring device 1640 in communications with the sensors of the strain gauges 1635 and/or the sensors of the strain gauge 1636. The external monitoring device 1640 may communicate with the sensors of the strain gauge 1635 and/or the sensors of the strain gauge 1636 using radio frequency communications. In various embodiments, the external monitoring device 1640 may communicate with the sensors of the strain gauge 1635 and/or the sensors of the strain gauge 1636 using wireless communications. For example, the external monitoring device 1640 may communicate with the sensors of the strain gauge 1635 and/or sensors of the strain gauge 1636 using electromagnetic or other energy fields to trigger the sensors or strain gauges and transmit the sensor measurement data to the external monitoring device 1640 or a remote server 1650.

In some embodiments, the external monitoring device 1640 may include a standalone electronic device located at the residence of the patient, hospital or other dwelling. The standalone electronic device may trigger the strain gauge 1635 and/or strain gauge 1636 to transmit the sensor data to the standalone electronic device, which may in turn transmit the sensor data to the remote server 1650 using the Internet or an Intranet or other communication protocols. The remote server 1650 may have a web-application running thereon to selectively serve graphical user interfaces to medical professionals, patients and patient's representatives or guardians.

The remote server 1650 may also be selectively accessible by the external monitoring device 1640 to receive data analytics of the monitored growth of a bone, differential growth of a bone, and/or the growth rate of the bone. The remote server 1650 may also be selectively accessible by the external monitoring device 1640 to receive data analytics associated with lung capacity. The external monitoring device 1640 may also be served data representative of the operational status of the GM sensing system 1602. Lung capacity may include lung function or ribcage/thorax volume.

The external monitoring device 1640 may include a communication device, such as a web-enabled smart phone or body-wearable computing device, such as embedded in a smart watch. For example, the cellphone, mobile communication device, or smart watch may transmit local sensor data to a remote server 1650. The external monitoring device 1640 may include a computing device, such as a laptop, personal computer, or tablet, or other electronic device, which may communicate sensor data to a remote server 1650. In various embodiments, the remote server may be omitted and the external monitoring device 1640 performs the data analytics.

In some embodiments, the surgical implant system 1600 may include graphical user interface(s) (GUIs) for displaying on a display of an external monitoring device 1640 data analytics associated with monitored sensor data. In various embodiments, the GUIs 1645 may provide a graphical representation of data analytics representative of a measured growth, differential growth or growth rate continuously or in periodic increments. The GUIs may provide a graphical representation of a notification or alert to the parent or guardian to seek medical attention or that intervention is needed. The GUIs 1645 may be compatible with various computing system platforms.

In various embodiments, the GM sensing system 1602 may include a plurality of strain gauges 1635, which may be configured to be embedded in one or more bones of a patient where growth, differential growth, and/or growth rate may be measured for the treatment of a bone deformity or bone disease, such as in a pediatric patient. In some embodiments, Each strain gauge 635 may include in an anchoring assembly 10, such as shown in FIG. 1 and one or more sensors 314a, 314b, 314c, and 314d (FIGS. 15A-15D). The sensors may be embedded in set screw 50, as described above. Each sensor may have its own unique identifier and location identifier. The system 1600 may be configured to access the data of a particular strain gauge 1635 to interrogate its sensors for sensor data.

In order to determine the longitudinal length between two or more bones, the system may use sensor data of two sensors that oppose each other, for example. The two sensors are in different strain gauges and may be coupled to the same longitudinal member device, for example. In order to determine the lung capacity, sensors coupled to opposite longitudinal member devices may be used to determine an expansion of the rib cage or thoracic cage.

The bone correction system 1620A may include a longitudinal member device 1630A (e.g., longitudinal member 100 of FIG. 1). In various embodiments, the longitudinal member device 1630A may include one or more strain gauges 1636, denoted as triangles, embedded in the body of the longitudinal member device 1630A.

The longitudinal member device 1630A may include a dynamically expandable rod 1630B as will be describe in FIG. 16B, a tether 1630C as will be described in FIG. 16C, a remotely controlled expandable rod 1630D as will be described in FIG. 16D, or other longitudinal member device.

Figure 16B:
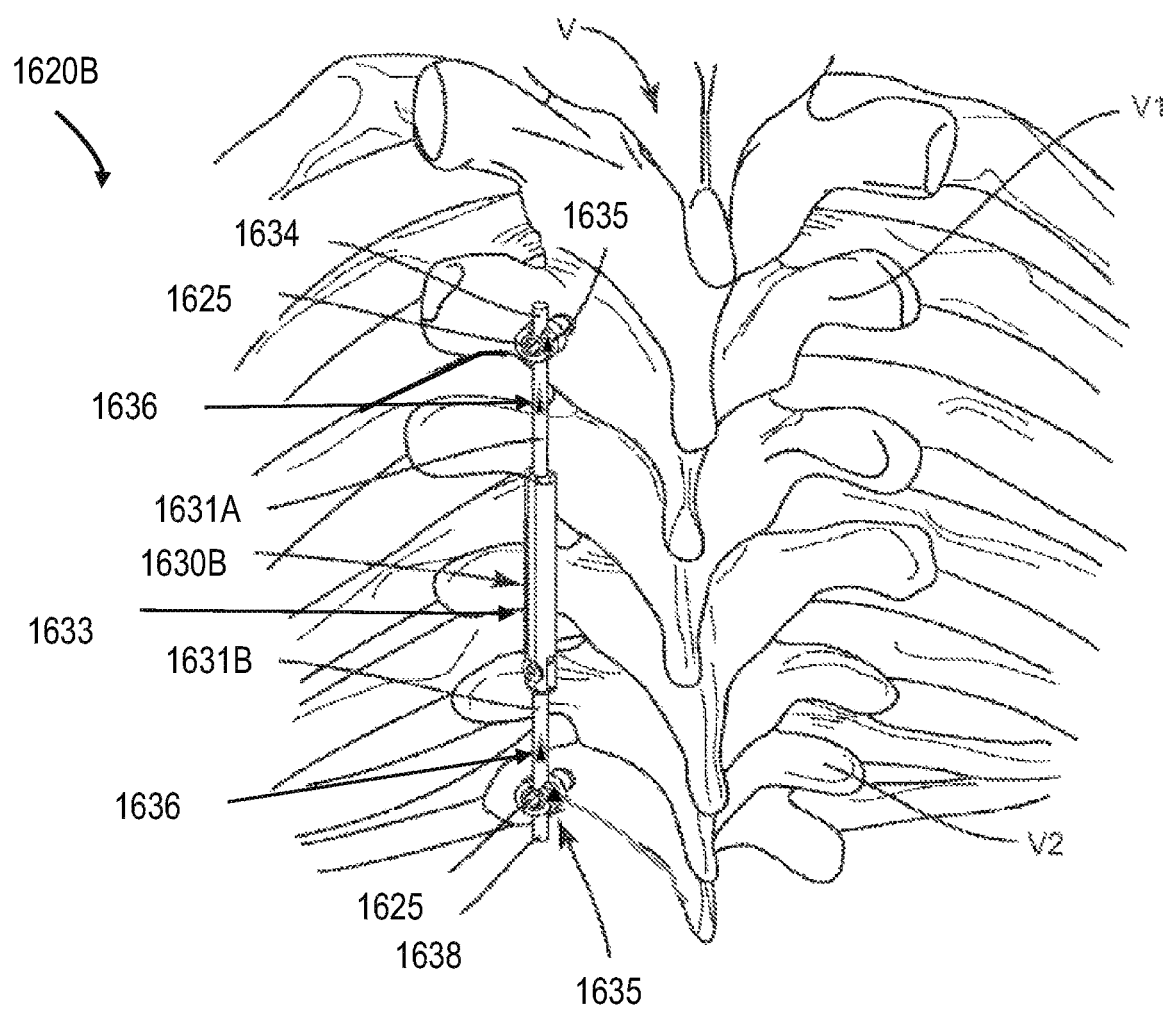
FIG. 16B is a perspective view of one particular embodiment of a bone correction system having a dynamically expandable longitudinal rod fastened to vertebrae associated with a rib cage.

FIG. 16B is a perspective view of one particular embodiment of a bone correction system 1620B having a dynamically expandable longitudinal rod 1630B fastened to vertebrae V1, V2 associated with a rib cage. An example, expandable rod is described in U.S. Pat. No. 10,456,171, entitled "SPINAL CORRECTION SYSTEM AND METHOD," assigned to Warsaw Orthopedic, Inc. and which is incorporated herein by reference in its entirety. The bone correction system 1620B may include two side-by-side expandable rods, one being concave and the other being convex.

The expandable longitudinal rod 1630B may include a rod sleeve 1633, a first rod element 1631A and a second rod element 1631B. In operation, the first rod element 1631A and a second rod element 1631B may telescope or extend out from ends of sleeve 1633 to increase or extend the length of rod 1630B.

The bone correction system 1620B may include a first fastening element, such as, for example, bone construct 1625 configured to attach to a first end 1634 of rod element 1631A to vertebra V1. The bone correction system 1620B may include a second fastening element, such as, for example, bone construct 1625 configured to attach a first end 1638 of rod element 1631B to vertebra V2, which is spaced apart over vertebrae from vertebra V1. Pilot holes are made in vertebrae V1, V2 for receiving bone constructs 1625. The other ends of the rod element 1631A and rod element 1631B are slidably coupled to opposite ends of sleeve 1633.

In various embodiments, the bone constructs 1625 may be torqued on to ends 1634, 1638 to attach the bone correction system 1620B in place with vertebrae V. In some embodiments, the bone constructs 1625 may include one or a plurality of hooks, anchors, tissue penetrating screws, monoaxial screws, multi-axial screws, expanding screws, wedges, buttons, clips, snaps, friction fittings, compressive fittings, expanding rivets, staples, nails, adhesives, fixation plates and/or posts. These fixation elements may be coated with an osteoinductive or osteoconductive material to enhance fixation, and/or include one or a plurality of therapeutic agents. These bone constructs 1625 may include a strain gauge 1635. The rod 1630B may include one or more strain gauges 1636. For example, the rod element 1631A, rod element 1631B and/or sleeve 1633 may include a strain gauge 1636.

Upon implantation of bone correction system 1620B and completion of the procedure, bone correction system 1620B is configured for in situ, non-invasive lengthening to compensate for patient growth. For example, during patient growth, an expansion force, due to separation of vertebrae V1, V2 attached to rod 1630B that causes dynamic incremental movement of the rod, relative to sleeve 1633 along a longitudinal axial direction.

In some embodiments, the rod may be configured to be extended using a magnetic field. In other embodiments, the rod may be configured to be extended using an electromagnetic field or electronically. In such an embodiments, the rod would be equipped with an integrated circuit and communication components to receive control signals from a remote source, as described above. The rod may include passive or active batteries as described above in relation to the load sensing assembly.

Figure 16C:
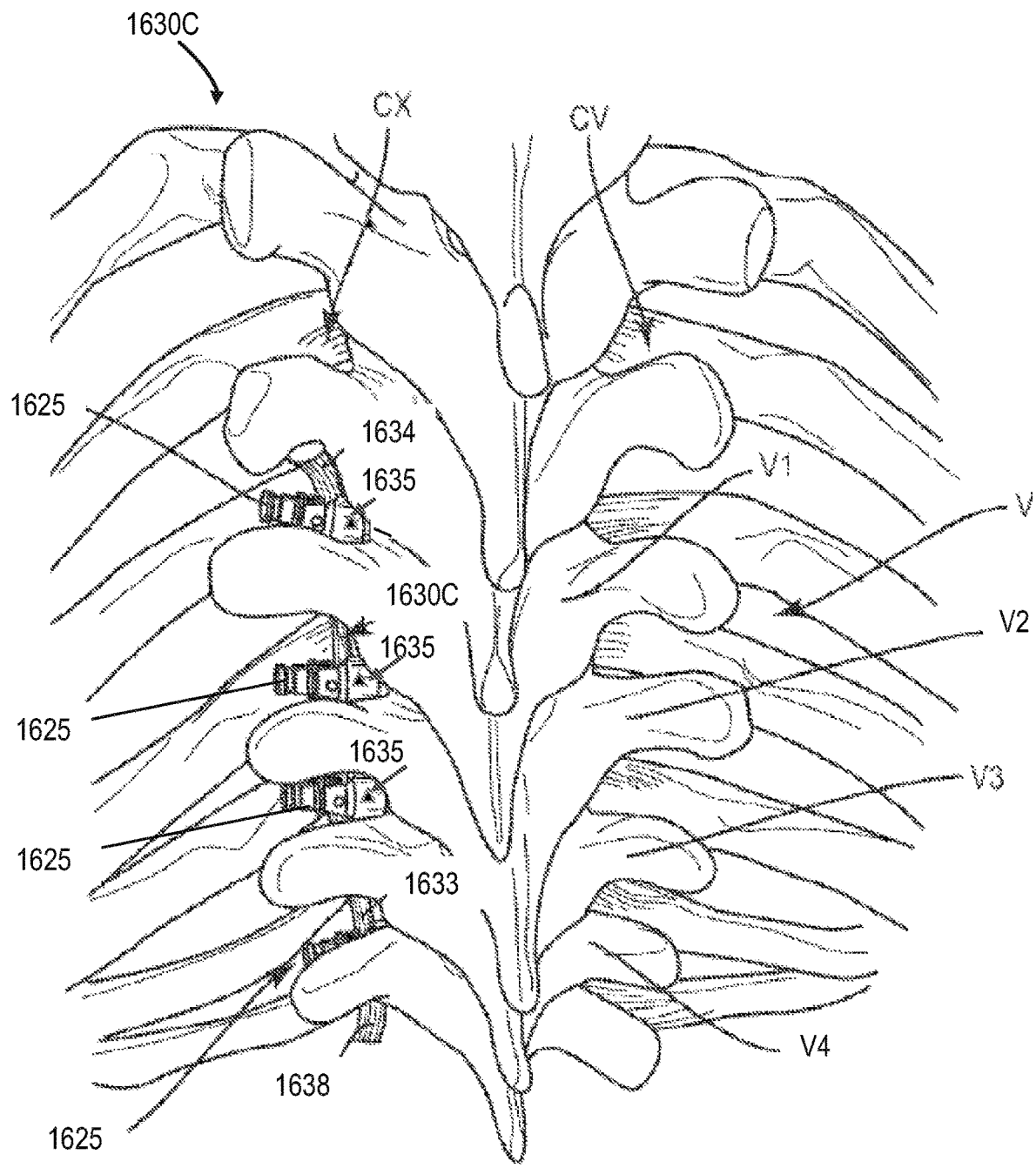
FIG. 16C is a perspective view of one particular embodiment of a bone correction system in accordance a fusionless system for vertebrae associated with a rib cage.

FIG. 16C is a perspective view of one particular embodiment of a (fusionless) bone correction system 1620C in accordance a fusionless system for vertebrae associated with a rib cage, such as disclosed in U.S. Pat. No. 9,220,536, entitled "SYSTEM AND METHOD FOR CORRECTION OF SPINAL DISORDER," assigned to Warsaw Orthopedic, Inc., incorporated herein by reference in its entirety. The bone correction system 1620C may include a longitudinal member device, such as, for example, a tether 1630C. In the example of FIG. 16C, CX denotes a convex side of the vertebrae column and CV denotes the concave side of the vertebrae column. Although not shown to prevent overcrowding in the figure, the bone correction system 1620C may include a longitudinal member device on both the convex side CX and the concave side CV.

The tether 1630C may include an elongated member 1633 that extends between a first end 1634 and a second end 1638. Tether 1630C may have a flexible configuration, which includes movement in a lateral or side-to-side direction and prevents expanding and/or extension in an axial direction upon fixation with vertebrae. In some embodiments, all or only a portion of tether 1630C may have a semi-rigid, rigid or elastic configuration, and/or have elastic properties such that tether 1630C provides a selective amount of expansion and/or extension in an axial direction. In some embodiments, the tether 1630C may be compressible in an axial direction. Tether 1630C can include a plurality of separately attachable or connectable portions or sections, such as bands or loops, or may be monolithically formed as a single continuous element.

Tether 1630C may have an outer surface and a uniform thickness/diameter. The outer surface may have various surface configurations, such as, for example, rough, threaded for connection with surgical instruments, arcuate, undulating, porous, semi-porous, dimpled, polished and/or textured according to the requirements of a particular application. The thickness defined by tether 1630C may be uniformly increasing or decreasing, or have alternate diameter dimensions along its length. The tether 1630C may have various cross section configurations, such as, for example, oval, oblong, triangular, rectangular, square, polygonal, irregular, uniform, non-uniform, variable and/or tapered.

The tether 1630C may have various lengths, according to the requirements of a particular application. It is further contemplated that tether 1630C may be braided, such as a rope, or include a plurality elongated elements to provide a predetermined force resistance. The tether 1630C may be made from autograft and/or allograft, as described above, and be configured for resorbable or degradable applications.

The bone correction system 1620C may include fixation elements, such as, for example, bone constructs 1625 that may be configured to be connected or attached with to tether 1630C. The bone correction system 1620C may include different types of fixation elements. The fixation elements or bone constructs 1625 are spaced along the length of tether 1630C and are configured to affix to the tether.

The fixation elements or bone constructs 1625 may be configured to connect to vertebrae along a plurality of vertebral levels. It is envisioned that the fixation elements may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. These fixation elements may be coated with an osteoinductive or osteoconductive material to enhance fixation, and/or include one or a plurality of therapeutic agents. The fixation elements may be fitted with a load sensing assembly as shown in FIG. 3, previously described.

In this example, the bone constructs 1625 of the growth modulating implants are implanted into bones V1-V4. The longitudinal growth may be measured, based on the sensors implanted in V1, V2, V3 and V4, between V1 and V2, V1 and V3, and V1 and V4. Likewise, a longitudinal growth may be measured between V2 and V3, V3 and V4 and V2 and V4. The signals from the implants on the concave and convex sides of the curve can determine if the curve is worsening, improving or the curve is being developed on the opposite side of the original curve. In this example a sensor that was reporting compression force may report tension, showing curve developed on the opposite side, or a higher compression or tension compared to a prior instance or the predicted value for a given time, meaning worsening of the curve, or the sensors on the concave and convex show similar change or rate of changes in the collected loading, taking the initial loading differences into account, showing a correction of the curve.

In assembly, operation and use, a fusionless correction system 1620C, similar to the system described above, is employed with a surgical procedure, such as, for a correction treatment to treat adolescent idiopathic scoliosis and/or Scheuermann's kyphosis of a spine. It is contemplated that one or all of the components of the fusionless correction system can be delivered or implanted as a pre-assembled device or can be assembled in situ. The fusionless correction system may be completely or partially revised, removed or replaced.

The fusionless correction system may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder. The configuration and dimension of tether 1630C is determined according to the configuration and dimension of a selected set of vertebrae and the requirements of a particular application.

The longitudinal member device may include one or a plurality of flexible wires, staples, cables, ribbons, artificial and/or synthetic strands, rods, plates, springs, and combinations thereof. In an embodiment, the longitudinal member device may be a cadaver tendon. In one embodiment, the longitudinal member device may be a solid core. In one embodiment, the longitudinal member device may be tubular.

Figure 16D:
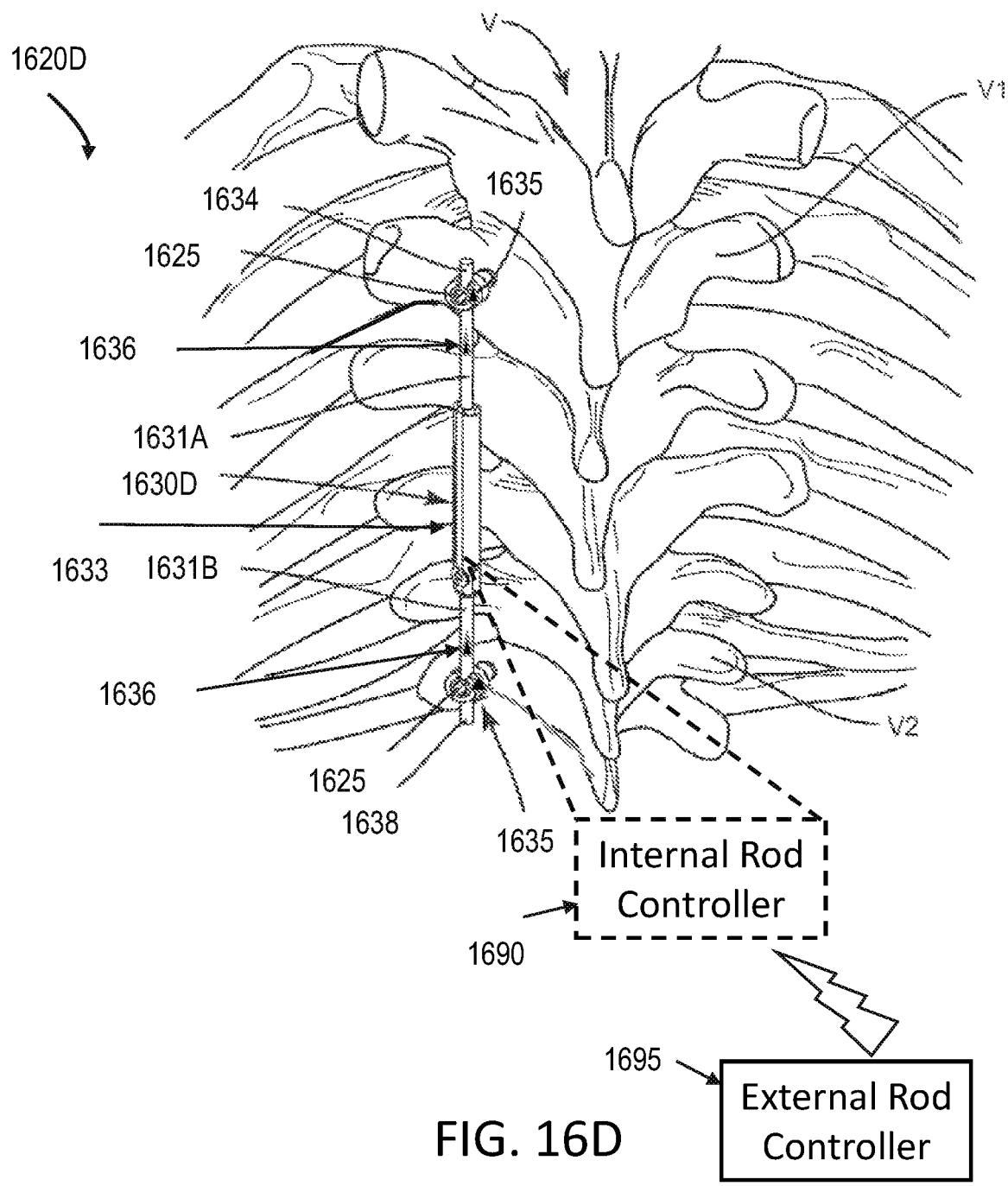
FIG. 16D is a perspective view of one particular embodiment of a bone correction system having a remotely expandable longitudinal rod fastened to vertebrae associated with a rib cage.

FIG. 16D is a perspective view of one particular embodiment of a bone correction system 1620D having a remotely expandable longitudinal rod 1630D fastened to vertebrae associated with a rib cage. The bone correction system 1620D is similar to the bone correction system 1620B described above. Thus, only the differences will be described. In FIG. 16D, the remotely expandable longitudinal rod 1630D may include a internal rod controller 1690 configured to control the telescopic motion of the first and second rod elements 1631A and 1631B. The internal rod controller 1690 may be response to and controlled by remote rod controller 1695. For example, the remote rod controller 1695 may provide a signal representative of the amount of extension to slide or telescope each of the first and second rod elements 1631A and 1631B. In some embodiments, the communication of the control signal may be magnetic. In other embodiments, the communication may electromagnetic or a radio frequency. The amount of correction of a longitudinal member device may be identified based on the intervention needed as derived from the sensor data.

The bone correction system 1620A, 1620B, 1620C or 1620D described above may each include a GM sensing system 1602, as previously described in relation to FIG. 16A. The GM sensing system 1602 may include a remote server 1650 and an external monitoring device 1640. The strain gauge 1635 and/or 1636 may communicate with the remote server 1650 and/or an external monitoring device 1640, as previously described.

The bone correction systems 1620A, 1620B, 1620C and 1620D may be spinal correction systems. The bone correction system is configured to be growth-friendly.

Figure 17:
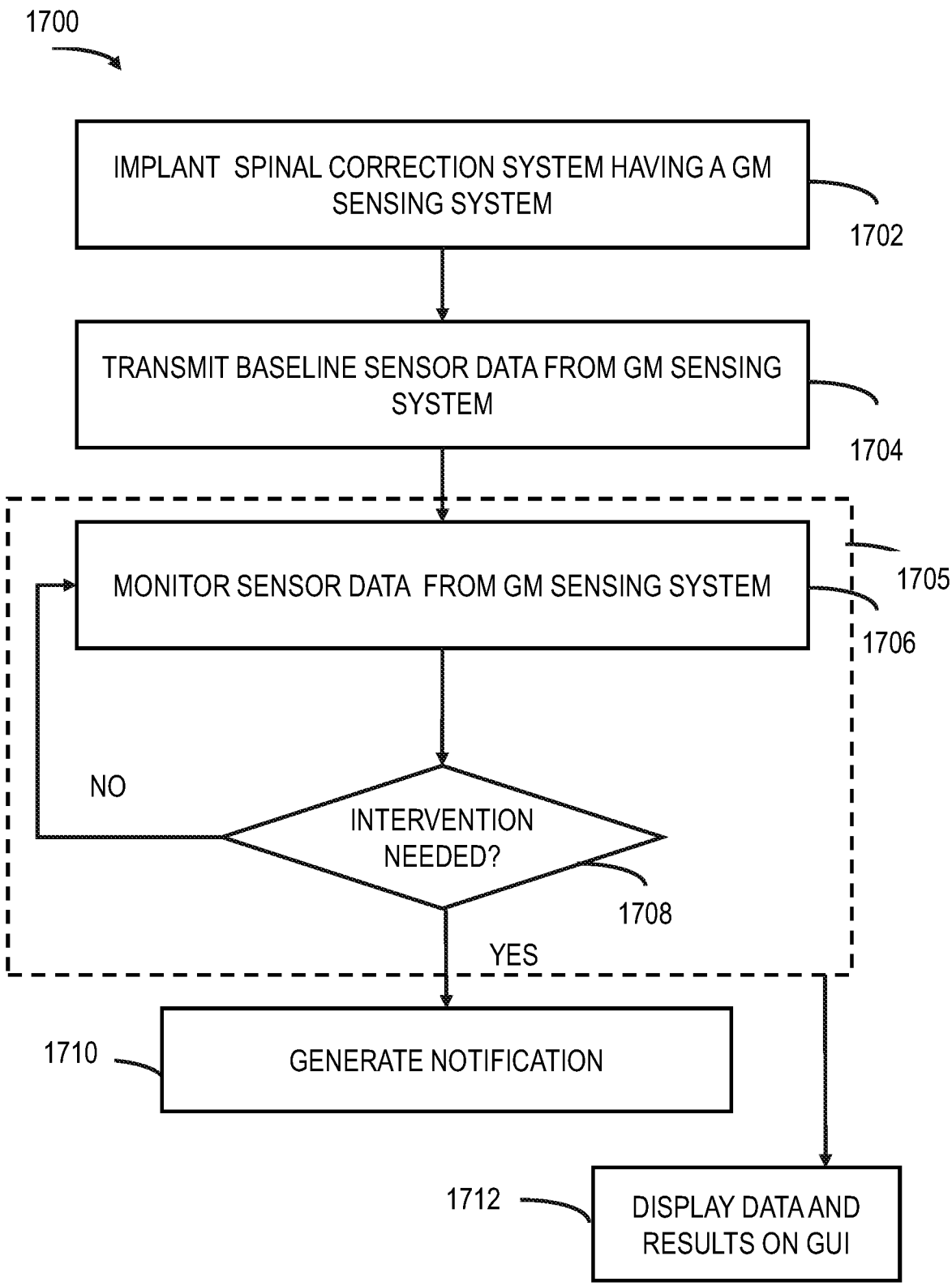
FIG. 17 illustrates an example flowchart of a method for treating a bone abnormality and monitoring growth features, correction progression or lung expansion.

FIG. 17 illustrates an example flowchart of a method 1700 for treating a bone abnormality and monitoring growth features, correction progression and/or lung capacity. The method steps, described herein, may be performed in the order shown or a different order. The method may include additional steps or some steps may be omitted. One or more steps of the method may be performed contemporaneously.

The method 1700 may include (at 1702) implanting bone correction system 1620A, 1620B, 1620C or 1620D, for example, having a GM sensing system 1602 into a subject bone using a growth-friendly or fusionless methodology. Some of the Implants (i.e., bone fastener 1625 or longitudinal member 1630) may include sensors of the GM sensing system 1602 used to collect loading data related to changes in the growing spine after the surgery during which such spinal implants may be fixed to the anatomical landmarks including, vertebral body, rib cage, and/or pelvis. These landmarks describe the insertion point of the implants. Implants may be placed in any of these sites based on the patient's need. If the longitudinal member device 1630A, expandable rod 1630B or 1630D or tether 1630C is connected to the ribs a real-time measurement can also report the lung expansion capacity. This measure in addition to growth can be used to generate an alarm for intervention.

The method 1700 may include (at 1704) transmitting baseline sensor data from the one or more sensors (e.g., sensors 314a, 314b, 314c, and 314d) of each strain gauge 1635 of bone construct 1625 and/or strain gauge 1636 of the longitudinal member device 1630A, 1630B or 1630C.

The method 1700 may include (at 1705) a monitoring and tracking process. The monitoring and tracking process may include (at 1706) monitoring the sensor data from the GM sensing system 1602. The monitoring and tracking process (at 1705) will be described in more detail in relation to FIG. 18. The method 1700 may include (at 1708) determining whether an intervention is needed. An intervention may require a revision surgery or a surgery to adjust the tension or compression in the current implant system for the treatment of the bone deformity or disease is needed, for example. The intervention may require replacement of an implant or longitudinal member device. Intervention may include scheduling a visit either a clinical visit or a surgeon visit. In some embodiment, an intervention may include canceling an already scheduled visit, if intervention is not required.

If the determination (at 1708) is "NO," monitoring continues (at 1706). If the determination (at 1708) is "YES," the method 1700 may include (at 1710) generating information representative of a notification that a fusion is necessary or an acceptable remedy for the treatment of the bone deformity or disease. For example, a notification that an intervention or clinical visit is needed may indicate one of tether replacement, rod expansion, revision surgery or removing and replacing the broken/fractured implant. The notification alerts may be sent to a doctor, a clinic, a patient, a patient representative or guardian, for example. If the lung capacity needs an intervention, a notification may be generated representative of the lung capacity and out-of-range indicator, for example. An intervention may include changing the position of the patient or check whether the rib cage is obstructed. The notification associated with the analyzed longitudinal growth or the growth rate may be based on patient specific data as determined from a patient's prior data, cohort specific data as determined from literature, or a combination of the patient specific data and the cohort specific data. The notification associated with the analyzed lung capacity or any other patient health parameter may be based on patient specific data as determined from a patient's prior data, cohort specific data as determined from literature, or a combination of the patient specific data and the cohort specific data.

Figure 18:
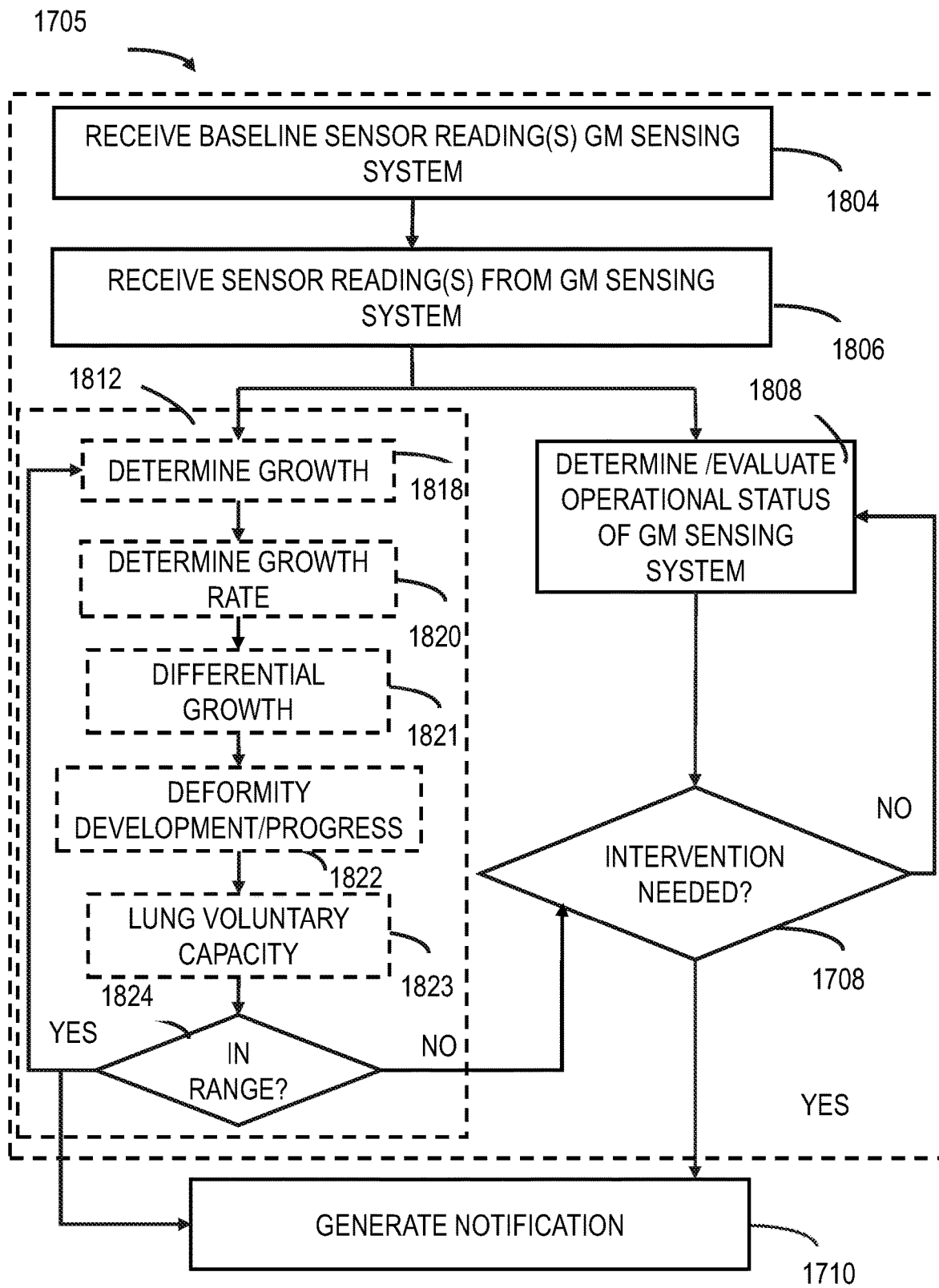
FIG. 18 illustrates an example flowchart for monitoring of bone growth, differential growth, growth rate, deformity development or progress, lung expansion or capacity and/or a system operational status.

FIG. 18 illustrates an example flowchart of a method 1705 for monitoring and tracking bone growth, differential growth, growth rate, deformity development or progress, lung capacity and/or a system operational status. The method 1705 will be described in relation to FIG. 16A. The sensor data and tracked bone longitudinal bone growth, differential growth, growth rate, deformity development, lung capacity may be selectively displayed (at 1712) in one or more GUIs. Additionally, the operation status of any one implant may be displayed as well.

As the growth rate varies between individuals, methods are needed to identify the optimal time of intervention to allow adequate growth or determine an interruption in growth modulation plan. For example, each child may experience a growth spurt according to their own body's progress. Hence, pinpointing the need for intervention, such as the result of a growth spurt, may be detected in real-time based on sensor data from the strain gauges or other sensors.

The monitoring of the growth, differential growth, growth rate and/or the operational status of the system may be performed by one or more computing systems. For example, data analytics of the sensor data may be performed by a remote server 1650 and served to the external monitoring device 1640. Alternately or in addition to, the external monitoring device 1640 may perform the data analytics and provide graphical user interfaces for display of the information representative of the resultant data analytics. The sensing system 1602 may monitor data associated with lung capacity or lung expansion if at least one rib or vertebra of the rib cage has an implant with a strain gauge implanted therein.

The method 1705 may include (at 1804) receiving baseline sensor data from the one or more sensors (e.g., sensors 314a, 314b, 314c, and 314d) of each bone construct 1625 and/or sensors of at least one stain gauge 1636 of the longitudinal member device 1630A, for example, of the GM sensing system 1602 at time of implantation. During surgery, the baseline sensor data may be sent to a storage device such as associated with a remote server or other computing device. The computing device performing data analytic may be configured to receive or discover all sensor data being read from the sensors of the GM sensing system 1602.

The method 1705 may include (at 1806) receiving sensor data from the one or more sensors (e.g., sensors 314a, 314b, 314c, and 314d) of each bone construct 1625 and/or sensors of at least one strain gauge 1636 of the longitudinal member 1630 of the GM sensing system 1602, periodically or continuously. As described above, the computing device performing data analytic may be configured to receive or discover all sensor data being read from the sensors of the GM sensing system 1602. In one embodiment the computing device translates the sensed data for example from a strain gauge to the rate of bone growth collected from various sensors, differential growth between two sensors, or remaining growth in the bone to facilitate interpretation. In another application, the sensed data can update the shape or alignment of the spine in an analytical model that corresponds to the changes in the sensed data. As such, the growth (increase in distance) and rotation (torsion in the longitudinal member or screw system) of the spine system can be visualized. The rotation may be generated into a two-dimensional (2D) or three-dimensional (3D) model.

The method 1705 may determine and evaluate the operational status of the GM sensing system 1602 (at 1808) implanted in a patient. The method 1705 may determine at least one patient health parameter of a patient (at 1812), as will be discussed in more detail in relation to FIGS. 19A-19C.

The method 1705 may determine and evaluate at least one of the growth (at 1818), growth rate (at 1820) differential growth (at 1821), bone deformity development and/or bone deformity progression (at 1822), and/or lung capacity (at 1823) associated with the patient. The method 1705 may determine the an improvement in the lung capacity when it reports a higher tension value during respiration cycle. On the other hand a lack of showing such tension from the sensor reading or a compressive force means a need for expansion of the longitudinal implants to allow growths and expand the distance between the ribs.

The increase in the spinal deformity severity may be determined as a measure of growth that is out-of-range for a period of time or in relation to the baseline sensor measurements. A decrease in the severity of the spinal deformity or a stable spinal deformity shown for example with no change in Cobb angle may use baseline sensor data and accumulative growth measurements, to identify an amount of correction. For example, sensor data from at least one the longitudinal member device may be used to identify the amount of deformity correction.

The blocks at 1818, 1820, 1822, and 1823 are dashed to denote that one or more of these block may be optional or omitted. For example, if the bone correction system 1620A, 1620B or 1620C may be affixed to a rib or vertebra of the thoracic spine, or one end may be affixed to the ribs and the other end to lumbar spine or pelvis, then the changes in lung capacity and/or expansion or a change in the spinal deformity, or spinal growth may be determined.

By way of non-limiting example, when two or more ribs are connected via a sensor enabled implant, the change in the sensor data from these implants may determine a change in the lung capacity. However, if one end of an implant system is also connected to the spine, a change in the reported sensor data may be because of the changes in the spinal deformity or growth combined with a change in the lung function.

The method 1705 may, in response to the determination (at 1808) of the operational status of the GM system 1602, determine (at 1708) whether an intervention is needed. In some instances, the growth modulating system (e.g., the bone correction system 1620A, 1620B or 1620C) experiences a component break, fracture, or loosening, an unexpected change that does not match the previous pattern of the data can be detected and reported.

The operational status of the GM sensing system 1602 may detect the operational status of a sensor, a strain gauge, each component of the loading sensing assembly (FIG. 3) or the implant. The strain gauge may produce an electrical signal. Differences in signal patterns may identify a fault, break, fracture, or other malfunction. If the determination (at 1708) is "NO," the method 1705 continues to evaluate the operational status of the GM system 1602 (at 1808). If the determination (at 1708) is "YES," the method 1705 may (at 1710) generate information representative of a notification or alert that an intervention or intervention process may be needed.

By way of non-limiting example, an intervention process may require an intervention process that recommends the replacement of an adjustable longitudinal member device, expandable rod or tether, as the adjustment range is approaching an upper limit of the manufacture-specific recommendation.

By way of non-limiting example, the operational status may evaluate the measurement of the sensors to evaluate the operational status of the function of the implant to treat the spine or the operational status of a sensor or strain gauge to perform the sensing function. Each of the implant, strain gauge and/or the sensors in the implant may have a within-normal limits operational range based on known manufacture-specific recommendations. Additionally, each component of the load sensing assembly (FIG. 3) may have an operational range status.

By way of non-limiting example, an intervention process may require a reversal of an adjustment, if an over adjustment condition is sensed. For example, sensed data from by the sensors of a strain gauge may determine that the implant in which the strain gauge is embedded is experiencing an out-of-range strain, pressure or loading.

By way of non-limiting example, an intervention process may require repair or replacement of one or more bone constructs 1625 or longitudinal member 1630, such as a revision surgery.

The method 1705 may determine (at 1824) whether one or more of growth, the growth rate, growth differential, deformity development or progress, and lung capacity are in an expected range. For example, in some embodiments, overall growth or growth rate can be determined from other bones, as well, that are not being treated or prior data or the same patients or age-, or gender-matched cohort. The patient's log of sensor data may include clinical measurements or other measurements of non-treated bones. If the sensor values are in range, a corresponding alert may be generated (at 1710) representative of an in range sensor readings.

If the determination (at 1824) is "YES," the method 1705 continues to evaluate the growth (at 1818) and/or growth rate (at 1820). If the determination (at 1822) is "NO," the method 1705 may generate (at 1710) information representative of a notification or alert that the growth, growth rate and/or growth differential is not in range. The intervention may include non-surgical plan for rod expansion, surgical planning for replacing the tether, revision surgery for implanting new rods, and/or replacing other broken or loose implants. The generation of the notification or alert generated may include generating a text message, an email or other notification to stored contact information and method of communicating. A revision surgery may require a longer longitudinal member device 1630A, for example. In various embodiments, an intervention process may include enlarging of the longitudinal member device by a change in dimension electronically, magnetically or electromagnetically. In other embodiments, the changes may be dynamic using mechanical mechanisms.

If the method 1705 determines deformity development or progress is not in range (at 1824), intervention may not be needed immediately, but an alert may still be generated (at 1710). However, if the deformity correction is not in range (at 1824), after a given amount of time, a different type of spine treatment may be needed. If the deformity correction is in range, a corresponding alert may be generated (at 1710) representative of an in range sensor readings.

If the method 1705 determines (at 1824) that the lung capacity, for example measured by lung maximum voluntary capacity, is not in range, (at 1708), an intervention may be determined to include additional monitoring of the breathing capability of the patient, patient may be scheduled for clinical visit or surgery to expand the growing rod that allows to increase the volume of the hemi-thorax or ribcage.

Figure 19A:
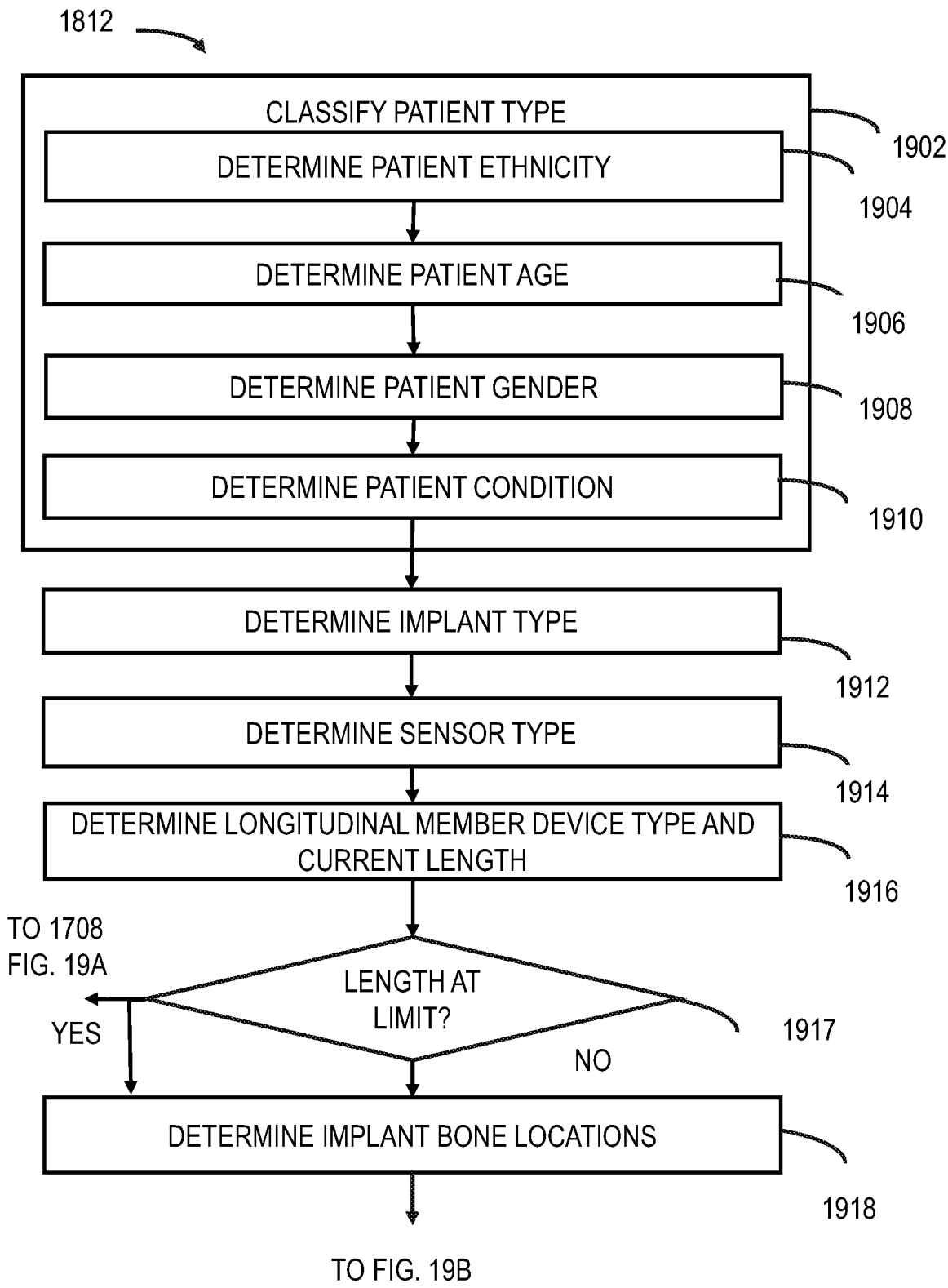
FIGS. 19A-19C illustrates an example flowchart of a method for analyzing at least one patient health parameter of a patient being treated by a bone correction system.
Figure 19B:
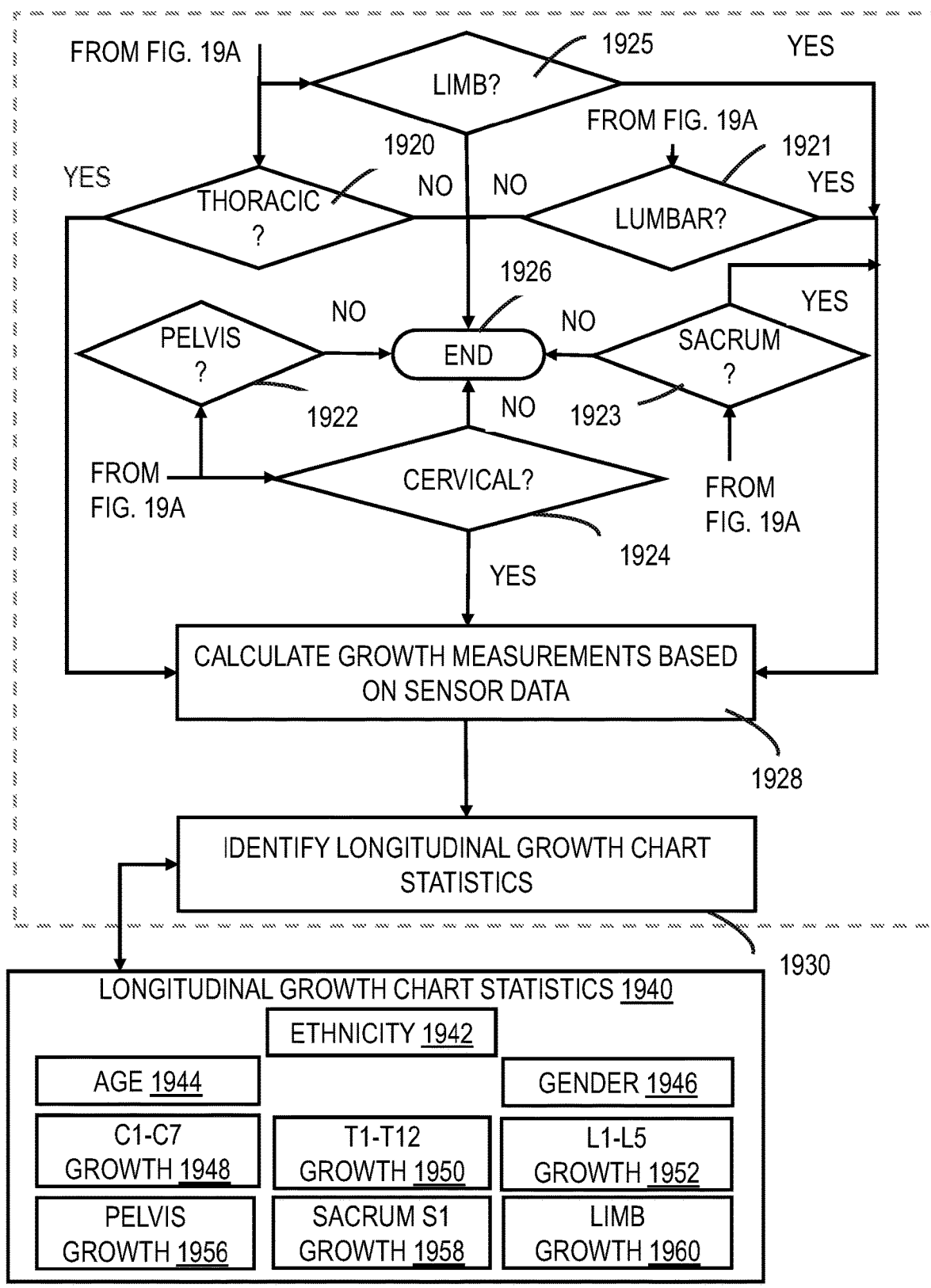
Figure 19C:
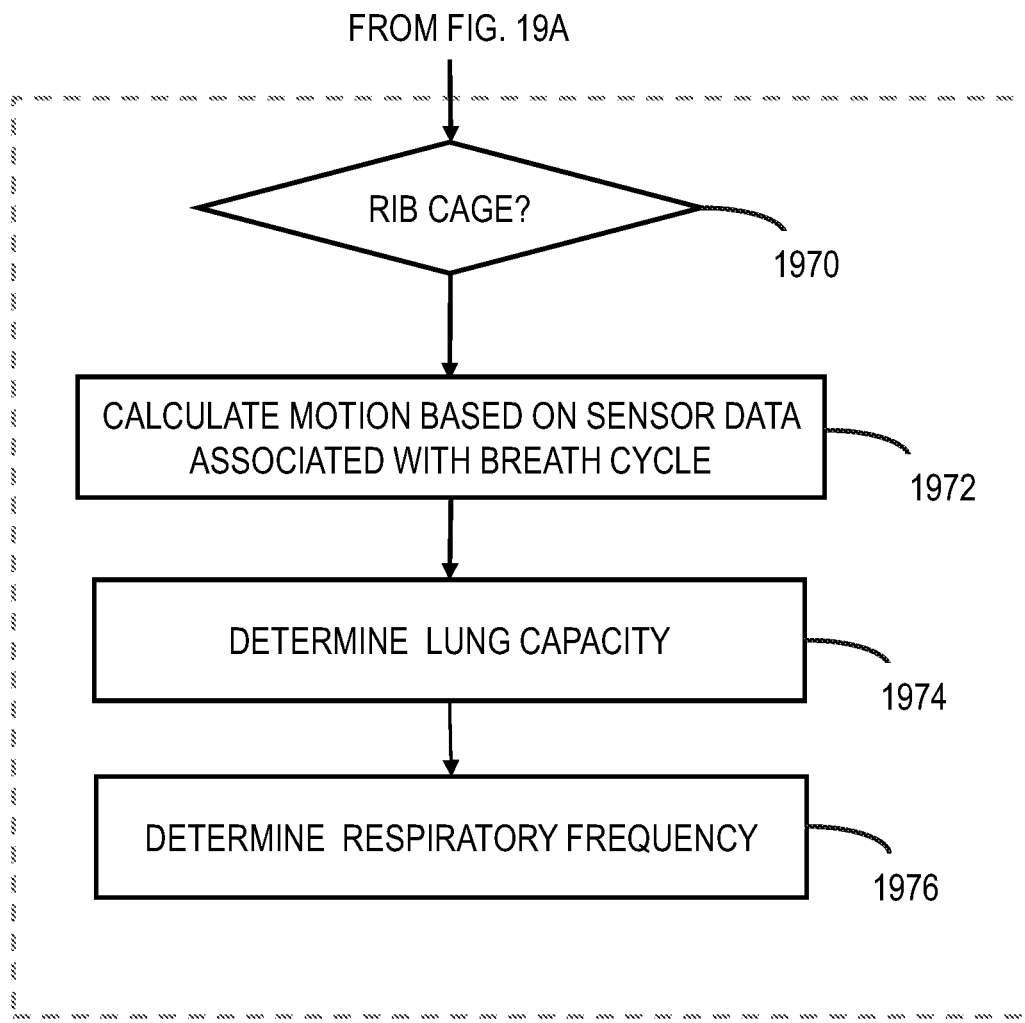

FIGS. 19A-19C illustrates an example flowchart FIGS. 19A-19C illustrates an example method 1812 for analyzing at least one patient health parameter of a patient being treated by a bone correction system (e.g., bone correction system 1620A, 1620B, or 1620C) using the surgical implant system 1600.

The method 1812 may include (at 1902) classifying patient type based on patient specific data. To classify the patient, certain patient data may be needed. For example, the method 1812 may include (at 1904) determining an ethnicity of the patient. The method 1812 may (at 1906) determine the patient's age. During the treatment phase using the bone correction system, the age will change. The method 1812 may include (at 1908) determining the gender of the patient. For example, a male child may grow at a different rate than a female child. The method 1812 may include (at 1910) determining a condition or co-morbidities, such as a spinal condition of the patient. For example, some children may have a spinal deformity, such as scoliosis or other curvature abnormalities. A patient may have multiple conditions, such as dwarfism and scoliosis. These conditions may be the cause of an out-of-range sensor readings. The patient may include both a spinal condition and a lung disease or condition. The classified patient data may be used to train a machine-learning algorithm for the classified patient type.

The method 1812 may include (at 1912) determining an implant type, such as a bone construct, anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. The implant type may have embedded in its body a strain gauge and/or load sensing assembly (FIG. 3). The method 1812 may include (at 1914) determining a sensor type. Each strain gauge may include a particular sensor type with identified sensing sensitivities. In some embodiments, each implant may include a plurality of sensors, such as without limitation a strain gauge sensor (i.e., force, pressure and/or tension sensor), impedance sensors, pressure sensors, capacitive sensors, and temperature sensors.

The method 1812 may include (at 1916) determining a longitudinal member device type, such as expandable rod, non-expandable rod, and/or tether. For example, rods with a fixed length may need revision quicker based on growth. In other embodiments, an expandable rod may be configured to expand to accommodate growth up to a predetermine limit set by the manufacturer's specification. In other embodiments, a tether may be configured to stretch up, if applicable, to a predetermined limit set by the manufacturer's specification. The system may track and determine (at 1916) the current length of the expandable rod or tether and provide a current length to external monitoring device 1640, in the form of an alert or notification. The sensors or strain gauges 1636 on a longitudinal member may be used to measure the expansion, such as the longitudinal growth, of the longitudinal member device. The method 1812 may include (at 1917) determining whether the current length is at or approaching the manufacturer's specified limit. If the determination is "YES," the method 1812 may determine if an intervention is needed. If so, an alert may be generated (at 1710) to identify the need to replace the longitudinal member device, for example. Intervention needed may identify the need to start surgical pre-planning phase for a revision surgery, for example. By way of non-limiting example, the pre-planning phase may include generating a new rod curvature based on current patient data.

The method 1812 may include (at 1918) determining implant bone locations or treatment locations. For example, one or more of the bone constructs may be implanted in two or more vertebrae. In some instances, the two or more vertebra may be in the same spinal section, such as thoracic, lumbar, cervical, or a combination of spinal sections. In some embodiments, the growth may be determined by a single implant comprising a strain gauge having a plurality of sensors arranged in space relation, as shown in FIGS. 15A-15E.

Referring now to FIG. 19B, the method 1812 may include determining whether any of the implant bone locations or treatment locations are associated with (at 1920) a thoracic vertebra, (at 1921) a lumbar vertebra, (at 1922) the pelvis, (at 1923) the sacrum, (at 1924) the cervical vertebra, and (at 1925) a limb. The pelvis may include three bones such as the hip bones, the sacrum and coccyx. Each bone location or treatment location may include a sensor or strain gauge. If the determination at 1920, 1921, 1922 and/or 1923 is "NO,"

the process will end (at 1926) for that bone, vertebra level, or section. If the determination at any of 1920, 1921, 1922, 1923, 1924 and/or 1925 is "YES," the method 1812 may include (at 1928) calculating an amount of longitudinal growth and/or a growth rate based each implant bone location and/or longitudinal member device. The growth rate is an amount of growth over a specified amount of time. The longitudinal growth may be measured between two bones, for example, separated by a longitudinal distance. The longitudinal growth may be the accumulative change in sensor data between the two bones, such as vertebra V1 and V2 of FIG. 16B when the sensors report the spatial position of the bone or a change in the stress in the longitudinal implant which in turn can be translated to the change in the deflection of the longitudinal implant and subsequently the distance between the implants attached to the bone. Based on the classified patient data, in-range threshold used at 1824 for the growth or growth rate may vary. The steps for determining the location of the bone implant locations along with the classified patient data may allow a machine-learning algorithm to be trained with statistics or training data for the patient classification type based on one or more of the patient's age, gender, ethnicity and co-morbidity.

Accordingly, the method 1812 may include (at 1930) identifying longitudinal growth chart statistics 1940 based on the patient classified data to classify a patient. The longitudinal growth chart statistics may include trained data sets for training the machine-learning algorithm. Pediatric patient's grow at a faster rate in certain age groups. Thus, the thresholds may be updated, accordingly. The method may track the patient's age so that the training data may be automatically updated from one instantiation to another, during the monitoring process. Example growth ranges by age group and gender are shown in described in "The growing spine: how spinal deformities influence normal spine and thoracic cage growth," by Alain Dimeglio, Eur Spine J (2012) 21:64-70, published online Aug. 30, 2011, incorporated herein by reference in its entirety. Example, measured growth in adolescence with scoliosis, is described in "Vertebral height growth predominates over intervertebral disc height growth in adolescents with scoliosis," by Ian Stokes Phd. et al., in National Institute of Health (NIH) Public Access, Spine (Phila Pa 1976), PMC 2006 Aug. 10, incorporated herein by reference in its entirety.

A trained data set may be correlated with both numerical sensor data from the training data set and training images of a population of subjects to determine longitudinal growth. To generate a training image, according to various embodiments, a representation may be labeled in an image or an entire image may be labeled. A labeled image may be an image that is identified to include the bone constructs, longitudinal member device and a pre-segmented portion (i.e., cervical vertebrae, thoracic vertebrae and/or lumbar vertebrae) of the training labeled image. The labeled image and sensor data, in conjunction or separately, may be used to train or allow a neural network, for example, to train and learn selected parameters, such as weights and biases in the bone correction system, based on type of longitudinal member device, type of bone construct and sensors. In some embodiments, the training data set of a current patient may be updated from time to time with values from segmented image data where a current longitudinal growth measurement is determined through imaging or sensor data.

In another embodiment, patient's own data may be used to train the machine learning algorithm. Data can be used from a patient who goes under several growing rod expansion to train the algorithm for the next consecutive expansion. After the first expansion, the sensor data can be recorded, until their next clinic visit. At the consecutive clinical visit, when a second rod expansion is scheduled, medical images including radiographs, ultrasound, dynamic MRI may be recorded and related to the sensor data. After the second expansion, the machine learning algorithm can use the sensor data and determine a possible change, which is normally concluded from the medical images, specific to that patient. This improves the predictive algorithm for that specific patient. Similarly, other patients with similar characteristics can benefit from such cohort-specific algorithm.

The longitudinal growth chart statistics 1940 may be used to identify for each implant location, an expected amount of growth or growth rate, an in-range threshold or out-of-range threshold, based on a patient's ethnicity 1942, age 1944, and gender 1946. The longitudinal growth chart statistics 1940 may include growth statistics for the cervical vertebrae C1-C7 1948, growth statistics for the thoracic vertebrae T1-C12 1950, growth statistics for the lumbar vertebrae L1-L5 1952, growth statistics for the cervical vertebrae C1-C7 1948, growth statistics for the pelvis 1956, and growth statistics for the sacrum S1 1958. A patient classification may identify the growth or growth rate. For example, a female patient in one age group may be expected to grow at a different rate than at a different age group. Likewise, a male patient in one age group may grow at a different rate than a female of the same age group. The embodiments described herein have application to limbs such as lower or upper limbs. The longitudinal growth chart statistics 1940 may include statistics associated with limbs 1960.

The method 1812 may generate alerts for both in-range results and out-of-range results (at 1710).

In some embodiments, the method 1812 when determining whether the analyzed health parameter is in-range, multiple parameters may be determined. For example, if the health parameter is growth or growth rate and if the bone or treatment locations include multiple locations, a growth differential between two implant locations in the same spine section may be determined, for example. Additionally, the growth or growth rate may be determined based on those bone or treatment locations in the same section, to report the growth or growth rate of a particular spine section. A growth differential may be determined based on two adjacent bone constructs that are connected to the same vertebra level, for example.

Referring now to FIG. 19C, the method 1812 may include (at 1970) determining whether any of the implant bone locations are attached to a rib cage and/or thoracic cage vertebra. The method 1812 may include (at 1972) determining motion or motion cycle of the rib cage and/or one or more vertebra of the thoracic cage. The motion or motion cycle may measure the expansion and contraction of the lungs as applied to one or more bones of the rib cage and/or vertebra of the thoracic cage using the strain gauge in the bone constructs and/or longitudinal member device. The rib cage moves out or extends during inhalation of a breath cycle and contracts when expiration occurs during the breath cycle. The method 1812 may include (at 1974) determining a patient's lung capacity. The motion of the rib cage or vertebra of the thoracic cage may be measured by the strain gauge, for example, during each breath cycle. A trained data set may be correlated with both numerical sensor data from the training data set and training images of a population of subjects to determine expected growth, lung capacity or ribcage/thorax volume. To generate a training image, according to various embodiments, a representation may be labeled in an image or an entire image may be labeled. A labeled image may be an image identified to include the bone constructs, longitudinal member device and/or a pre-segmented portion (i.e., thoracic vertebrae and/or ribcage) of the training labeled image to which the implants are attached. The trained data set may include disc growth, as well, derived from images. The labeled image and sensor data may be used to train or avow a neural network, for example, to train and learn selected parameters, such as weights and biases in the bone correction system, based on type of longitudinal member device, type of bone construct, sensor arrangement of strain gauge and/or sensors. In some embodiments, the training data set of a current patient may be updated from time to time with segmented image data where current lung capacity measurements may be determined through imaging relative to the actual thoracic ratios and symmetry between left and right thoracic ratios. Example, thoracic ratios by gender and age are described in "A segmental analysis of thoracic shape in chest radiographs of children. Changes related to spinal level, age, sex, side and significance for lung growth and scoliosis," by Theodoros Grivas et al., in J. Anat. 1991, 178, pp. 21-38, incorporated herein by reference in its entirety. Example, variances between the rib cage and thoracic spine morphology is described in "Association between rib shape and pulmonary function in patients with Osteogenesis Imperfecta," by Juan Sanchis-Gimeno et al., J. of Advanced Research 21 (2020) 177-185, incorporated herein by reference in its entirety. Example of gender differences in the thoracic vertebrae is described in "Sex differences in thoracic dimensions and configuration," by Francois Bellemare et al., Am. J. of Respiratory and Critical Care Medicine, vol. 168, 2003, pp. 305-312, incorporated herein by reference in its entirety. Lung function changes in childhood to adolescence are also described in "Lung function changes from childhood adolescence: a seven-year follow-up study," Pavilio Piccioni et al., BMC Pulmonary Medicine (2015) 15:31, incorporated herein by reference in its entirety.

The machine-learning algorithm may be trained with rib cage expansion and contraction measurements based on the sensor data of the strain gauge from patients with similar conditions, age, size and gender, for example. The machine-learning algorithm may be trained with rib cage expansion and contraction measurements from a universal set of patients. The classified patient data may adjust the in-range threshold used at 1824 for the current classified patient data. Although, the in-range threshold may be acceptable for a current patient, an alert or notification may still be generated (at 1710) of the current sensor readings and selected threshold. In some embodiments, a minimum threshold may be used for lung capacity, for example measured by lung maximum voluntary capacity. Additionally, the method 1812 may include (at 1976) determining a respiratory frequency. The patterns in sensor data used for expansion and contraction may also be used to determine respiratory frequency. Detection of changes in the frequency may be a sign of distress. Accordingly, at 1824, an in-range threshold may be set to determine if the frequency is in range.

The methods 1700, 1705, and 1812 may be implemented using hardware, firmware, software or a combination of any of these. For instance, methods 1700, 1705, and 1812 may be implemented as part of a microcontroller, processor, and/or graphics processing units (GPUs) and an interface with a register, data store and/or memory device 2020 (FIG. 20) for storing data and programming instructions 2022, which, when executed, performs the steps of methods 1700, 1705, and 1812 described herein.

Implants (e.g., bone constructs 1625 and/or longitudinal member 1630) transmit information to a receiver and processing unit that enables data visualization, analyses, and computation. The GM sensing system 1602 may use inferred or learned information from sensor measurements, for example, the variation in the measurements that can be deterministic of a change in the growth, growth rate, or the implant set itself that requires intervention.

Machine-learning algorithms may use the loading information, such as from a strain gauge, as a function of time and learn the patterns of loading in different locations of the spine and as well as the pattern of changes in such loading over time for various pathologies, age groups, and implant types. Such changes can be learned by a predictive model as the data being accumulated to predict a need for intervention or alarm a problem with the implant of the GM sensing system 1602.

Sensors or strain gauges directly or indirectly attached to the rib cage can identify a change in the respiration and generate a notification for intervention. The intervention may include straightening the spine or expanding the rib cage to increase the required volume for the lungs. For example, the continuous data monitoring may identify the maximum/minimum loading in each respiration cycle. An alarm may be generated when such loading in a particular respiration cycle starts to diminish, a change in the lung capacity can be identified by data logging of sensor measurements associated with the rib cage or thoracic cage.

The sensor data or sensor measurements may include a time stamp, at which the measurement data is recorded with reference to the surgery time and may be collected continuously or at specific times after surgery. Patterns representative of changes in the recorded measurement data may be learned by a machine-learning algorithm.

Such machine-learning algorithm may then predict, as a function of the reported measurements in comparison to both the prior measurements and the baseline values, the time at which an intervention is required due to the growth or complications with the implants of the GM sensing system 1602. The GM sensing system 1602 may measure, store, and report the data as a function of time. This means that at a given day, month, year or hour of the day or any time in between the sensed data can be recorded. As such, the linkage between the sensed data and the time, along with other patient specific parameters, for example, gender, age, therapy, and other co-morbidities can predict the sensed data as a given time, for example in one week. The machine-learning algorithm may determine that a measured value, in an upcoming future, by one or more sensors are higher than the expected measurement, identifying unexpected increase in the system's strain due to growth, lower than expected value, identifying lack of tension due to loosening or breakage/rupture, in one or more implants of the GM sensing system 1602 or does not match the trend or pattern of changes in such measurement indicating a change in the system that required medical intervention. The machine-learning algorithm may use data points over a period of time to identify a pattern of changes in the sensor measurement data and predict the value of such measurements at a later time. A discrepancy in the predicted value and the measured value above a predetermined threshold signals a need for clinical or surgical intervention and enables pre-planning for such intervention.

The machine-learning algorithms may employ supervised machine learning, semi-supervised machine learning, unsupervised machine learning, and/or reinforcement machine learning. Each of these listed types of machine-learning algorithms is well known in the art.

Figure 20:
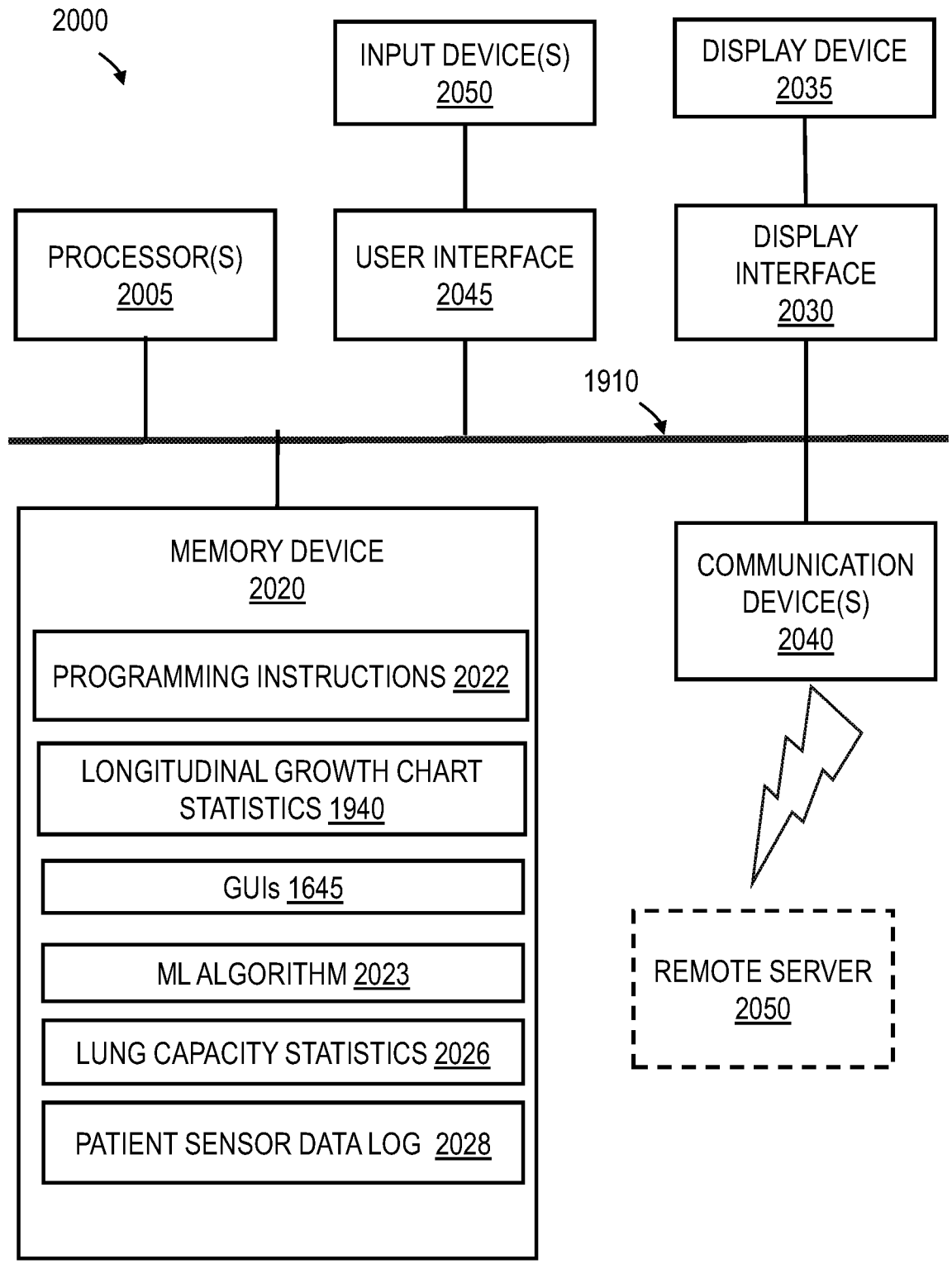
FIG. 20 illustrates an example of internal hardware that is included in any of the electronic components of an external electronic device.

FIG. 20 depicts an example of internal hardware that may be included in any of the electronic components of an electronic device 2000 as described in this disclosure such as, for example, a computing device, a remote server, cloud computing system, external electronic device and/or any other integrated system and/or hardware that may be used to contain or implement program instructions.

The system 1600 may store, in a memory device 2020 of FIG. 20, the operational status data of the GM sensing system 1602, the growth of each monitored bone and the growth rate of the at least one bone. Data analytics of the received measurement data may include trending data of the operational status data of the GM sensing system 1602. Data analytics of the received measurement data may include growth and the growth rate of one or more bones, each of which may each be displayed in a GUI (at 1712), as numerical values and/or as graphical data. In a situation that multiple bones are monitored such as in a vertebral column, each bone or vertebrae, each segment (cervical, thoracic or lumbar) of bones, and/or the collection of bones being monitored in the vertebral column may be individually monitored such that graphical representations of the status of each of these may be selectively displayed in a GUI (at 1712). For example, growth and/or growth rate of a particular vertebra may be displayed in a GUI (at 1712). The growth and/or growth rate of a particular segment of the vertebral column may be selectively displayed in a GUI (at 1712), especially, those vertebrae that are being treated. The growth and/or growth rate of all monitored bones in the vertebral column may be selectively displayed in a GUI (at 1712).

The GUIs may include GUIs 1645 (FIG. 16A) that may be configured to display a growth chart or three-dimensional (3D) diagram of one or more of the cervical section, the thoracic section and the lumbar section, for example, A growth chart of a vertebra section may be selected by a user using the GUI 1645. The GUIs 1645 (FIG. 16A) may display lung capacity in the form of a 3D diagram of the rib cage expanding, for example, and/or a graph of the changes in lung capacity over time. The data in the GUIs is updated based on the user selection and real-time sensor data.

The memory device 2020 may store the longitudinal growth chart statistics 1940. The memory device 2020 may include machine-learning algorithms 2023 for analyzing the sensor data based on trained data for classified patients. The machine-learning algorithms 2023 may include a predictive algorithm that predicts when and how much correction in the bone correction system is required using the sensor data and patient specific parameters. For example, a correction system may use an expandable rod that is selectively adjusted to expand the length of the rod such as using a magnetic field. The predictive algorithm may predict an amount of expansion in the rod is needed. The amount of magnetic field to be applied to the rod may be a function of the predicted amount of correction to expand the length of the rod. The rod expansion may be based on manufacturer's recommendations and growth. The machine-learning algorithms 2023 may include a neural network such as artificial neural network (ANN) and convolution neural network (CNN), by way of non-limiting example.

The memory device 2020 may include lung capacity statistics 2026 associated with rib cage expansion and contraction during a breath inhalation and expiration phases based on one or more of patient condition, age, gender, size, and/or co-morbidities or a patient's classification. The memory device 2020 may include a patient's sensor data log 2028.

A bus 2010 serves as the main information highway interconnecting the other illustrated components of the hardware. Processor(s) 2005 may be the central processing unit (CPU) of the computing system, performing machine-learning algorithms, calculations and logic operations as may be required to execute a program. CPU 2005, alone or in conjunction with one or more of the other elements disclosed in FIG. 20, is an example of a processor as such term is used within this disclosure. Read only memory (ROM) and random access memory (RAM) constitute examples of tangible and non-transitory computer-readable storage media, memory devices 2020 or data stores as such terms are used within this disclosure. The memory device 2020 may store an operating system (OS) of the computing device, a server or for the platform of the electronic device.

Program instructions, software or interactive modules for providing the interface and performing any querying or analysis associated with one or more data sets may be stored in the computer-readable storage media (e.g., memory device 2020). Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 2030 may permit information from the bus 2010 to be displayed on the display device 2035 in audio, visual, graphic or alphanumeric format. Communication with external devices may occur using various communication ports 2040. A communication port 2040 may be attached to a communications network, such as the Internet or an intranet. In various embodiments, communication with external devices may occur via one or more short range communication protocols. The communication port or devices 2040 may include communication devices for wired or wireless communications and may communicate with a remote server 1650. By way of non-limiting example, when in proximity, the external monitoring device 1640 may receive the sensor data from the GM sensing system and then communicate the sensor data to a remote server 1650 via communication devices 2040.

The hardware may also include a user interface 2045, such as a graphical user interface (GUI), that allows for receipt of data from input devices, such as a keyboard or other input device 2050 such as a mouse, a joystick, a touch screen, a remote control, a pointing device, a video input device and/or an audio input device. The GUIs, described herein, may be displayed using a browser application being executed by an electronic device and/or served by a server (not shown). For example, hypertext markup language (HTML) may be used for designing the GUI with HTML tags to the images of the patient and other information stored in or served from memory of the server (not shown).

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

In one or more examples, the described techniques and methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that may be used to store desired program code in the form of instructions or data structures and that may be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

As used herein, the term "about" in reference to a numerical value means plus or minus 10% of the numerical value of the number with which it is being used.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A method, comprising:
   implanting growth modulating implants of a bone correction system in two or more bones of a vertebral column or rib cage of a patient, wherein each growth modulating implant includes an implant body having at least one sensor device embedded in the implant body;
   receiving, by a processor, sensor data from the sensor devices associated with the two or more bones;
   determining, by the processor, an operational status of the growth modulating implants, based on the received sensor data;
   determining, by the processor, a lung capacity or a change in lung capacity, based on the received sensor data;
   determining, by the processor, a longitudinal growth or growth rate between the two or more bones, based on the received sensor data; and
   causing, by the processor, a display device to selectively display a graphical user interface (GUI) representative of at least one of the lung capacity, the change in lung capacity, the longitudinal growth, and the growth rate between the bones.

2. The method of claim 1, wherein:
   the processor is in a remote server; and
   further comprising:
   receiving the sensor data by an external monitoring device in proximity to the sensor devices, and
   transmitting the sensor data by the external monitoring device to the remote server.

3. The method of claim 1, further comprising:
   generating, by the processor, a notification representative of:
   the operational status of the growth modulating implants; or
   an intervention process based on the longitudinal growth or the growth rate between the two or more bones.

4. The method of claim 1, further comprising:
   analyzing, by the processor, the operational status of one or more of the sensor devices;
   determining, by the processor, that an intervention to correct at least one growth modulating implant is needed; and
   generating, by the processor, information representative of the needed intervention, in response to determining that the intervention is needed.

5. The method of claim 1, further comprising:
   analyzing, by the processor, the received sensor data from sensor devices of the growth modulating implants;
   determining, by the processor, deformity development or deformity correction of the two or more bones; and
   causing, by the processor, the display device to selectively display data representative of the deformity development or deformity correction of the two or more bones.

6. The method of claim 1, wherein the bone correction system further comprises a longitudinal member device comprising a flexible tether coupled to the growth modulating implants.

7. The method of claim 6, wherein the longitudinal member device has an adjustable length; and
   further comprising:
   enlarging the longitudinal member device coupled to the sensor devices based on the longitudinal growth.

8. The method of claim 1, further comprising:
   classifying, by the processor, the patient by patient type;
   retrieving, by the processor, trained classified patient data based on the classified patient type;
   analyzing, by the processor, using a machine-learning algorithm with the trained classified patient data, the longitudinal growth or the growth rate between the two or more bones; and
   generating a notification associated with the analyzed longitudinal growth, the growth rate or the lung capacity.

9. A system, comprising:
   a bone correction system comprising growth modulating implants being configured to be implanted in two or more bones;
   a growth monitoring (GM) sensing system comprising at least one sensor embedded in each growth modulating implant;
   an electronic device that comprises a processor and a non-transitory and tangible computer readable storage medium having programming instructions stored thereon, which when executed causes the processor to:
   receive sensor data from the sensor devices associated with the two or more bones;
   determine an operational status of the growth modulating implants, based on the received sensor data;
   determine deformity development based on the received sensor data;

determine a longitudinal growth or growth rate between the two or more bones, based on the received sensor data;

cause a display device to selectively display a graphical user interface (GUI) representative of at least one of the deformity development, the longitudinal growth, and the growth rate of the patient; and in response to the deformity development not being in an expected range, cause the display device to display an alert indicating that the deformity development is out of range.

10. The system of claim 9, wherein:

the processor is in a remote server; and further comprising programming instructions, which when executed causes the processor to:

receive the sensor data by an external monitoring device in proximity to the GM system, and transmit the sensor data by the external monitoring device to the remote server.

11. The system of claim 10, further comprising at least one of a personal communication device or the external monitoring device configured to:

directly receive the sensor data using short-range communications;

transmit the sensor data to the remote server; and selectively display on the GUI the longitudinal growth or the growth rate.

12. The system of claim 11, wherein the personal communication device comprises a web-enabled smart phone or body-wearable computing device.

13. The system of claim 9, further comprising programming instructions, which when executed causes the processor to:

analyze the received sensor data from sensor devices of the growth modulating implants;

determine deformity development or deformity correction of the two or more bones; and cause the display device to selectively display data representative of the deformity development or deformity correction of the two or more bones using the GUI.

14. The method of claim 9, wherein the bone correction system further comprises a longitudinal member device comprising a flexible tether coupled to the growth modulating implants.

15. The system of claim 14, wherein the longitudinal member device has an adjustable length; and further comprising:

an external rod controller configured to enlarge the longitudinal member device based on the longitudinal growth.

16. The system of claim 9, further comprising programming instructions, which when executed causes the processor to:

classify the patient by patient type;

retrieve trained classified patient data based on the classified patient type;

analyze using a machine-learning algorithm with the trained classified patient data, the longitudinal growth or the growth rate between the two or more bones; and generate a notification associated with the analyzed longitudinal growth or the growth rate based on patient specific data as determined from a patient's prior data, cohort specific data as determined from literature, or a combination of the patient specific data and the cohort specific data.

17. The system of claim 16, further comprising programming instructions, which when executed causes the processor to predict when and how much correction in the bone correction system is required based on the sensor data and the classified patient type.

18. The system of claim 17, further comprising programming instructions, which when executed causes the processor to generate an alarm for scheduling a medical visit either clinical or surgical or canceling an already scheduled visit, if intervention is not required.

* * * * *